(12) United States Patent
Malackowski et al.

(10) Patent No.: US 8,784,415 B2
(45) Date of Patent: Jul. 22, 2014

(54) POWERED SURGICAL TOOL WITH AN ISOLATION CIRCUIT CONNECTED BETWEEN THE TOOL POWER TERMINALS AND THE MEMORY INTERNAL TO THE TOOL

(75) Inventors: Donald W. Malackowski, Schoolcraft, MI (US); Paul M. Hoekstra, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 1399 days.

(21) Appl. No.: 12/435,905

(22) Filed: May 5, 2009

(65) Prior Publication Data

US 2009/0275940 A1 Nov. 5, 2009

Related U.S. Application Data

(60) Provisional application No. 61/050,430, filed on May 5, 2008.

(51) Int. Cl.
*A61B 18/14* (2006.01)

(52) U.S. Cl.
USPC ........................................... 606/42

(58) Field of Classification Search
USPC ......................... 606/27, 34, 41, 42
See application file for complete search history.

(56) References Cited

U.S. PATENT DOCUMENTS

| | | | | |
|---|---|---|---|---|
| 4,818,954 A | * | 4/1989 | Flachenecker et al. | 331/183 |
| 5,312,401 A | * | 5/1994 | Newton et al. | 606/46 |
| 5,334,183 A | * | 8/1994 | Wuchinich | 606/46 |
| 5,400,267 A | | 3/1995 | Denen | |
| 5,697,909 A | * | 12/1997 | Eggers et al. | 604/114 |
| 6,017,354 A | | 1/2000 | Culp et al. | |
| 6,074,386 A | | 6/2000 | Goble | |
| 6,248,126 B1 | * | 6/2001 | Lesser et al. | 607/113 |
| 6,308,089 B1 | * | 10/2001 | von der Ruhr et al. | 600/338 |
| 6,346,106 B1 | * | 2/2002 | Jako | 606/47 |
| 6,611,793 B1 | * | 8/2003 | Burnside et al. | 702/183 |
| 6,652,514 B2 | * | 11/2003 | Ellman et al. | 606/37 |
| 6,666,860 B1 | * | 12/2003 | Takahashi | 606/34 |
| 6,913,087 B1 | | 7/2005 | Brotto et al. | |

(Continued)

FOREIGN PATENT DOCUMENTS

| | | |
|---|---|---|
| DE | 102005044918 A1 | 2/2007 |
| EP | 1201196 A1 | 5/2002 |
| WO | 9940856 A1 | 8/1999 |
| WO | 2008/134358 A1 | 11/2008 |

OTHER PUBLICATIONS

EPO ISA Search Report and Written Opinion for PCT App. No. PCT/US2009/042739, Jul. 2009.

(Continued)

*Primary Examiner* — Michael Peffley
*Assistant Examiner* — Daniel Fowler

(57) ABSTRACT

A surgical tool system with a powered tool that includes a memory in which data describing the characteristics of the power signals that are to be sourced to the toll are stored. A control console based on the data in the tool memory sources the power signal to the tool. Both the data signals written out from the tool memory and the power signals from the console are exchanged over common console terminals and common tool terminals. An isolation circuit in the tool prevents the applied power signals from the console from adversely effecting the tool memory.

27 Claims, 19 Drawing Sheets

(56) References Cited

U.S. PATENT DOCUMENTS

| | | |
|---|---|---|
| 7,238,010 B2 | 7/2007 | Hershberger et al. |
| 7,422,582 B2 | 9/2008 | Malackowski et al. |
| 2003/0093103 A1 | 5/2003 | Malackowski |
| 2003/0204185 A1* | 10/2003 | Sherman et al. .................. 606/41 |
| 2005/0283148 A1* | 12/2005 | Janssen et al. ................... 606/34 |
| 2006/0030845 A1* | 2/2006 | Leung et al. ..................... 606/41 |
| 2007/0016185 A1 | 1/2007 | Tullis et al. |
| 2009/0171342 A1* | 7/2009 | Klimovitch et al. ............ 606/34 |

OTHER PUBLICATIONS

European Patent Office, "International Preliminary Report on Patentability for PCT/US2009/042739", May 3, 2010.

* cited by examiner

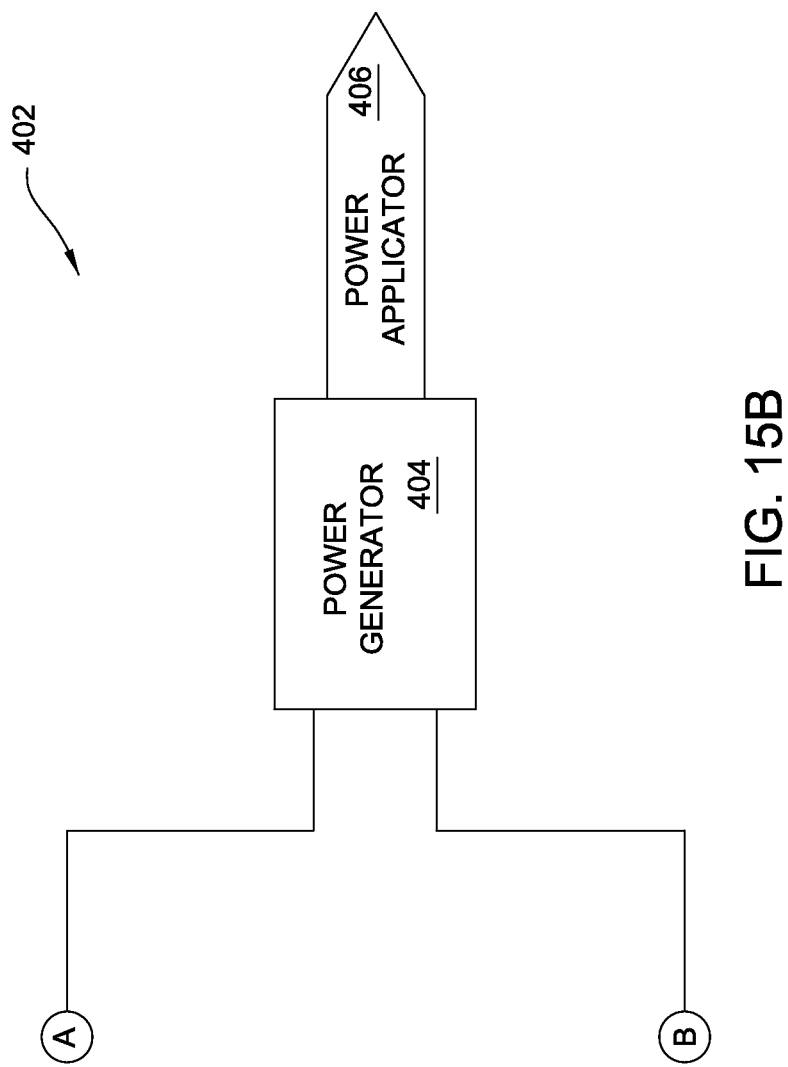

US 8,784,415 B2

POWERED SURGICAL TOOL WITH AN ISOLATION CIRCUIT CONNECTED BETWEEN THE TOOL POWER TERMINALS AND THE MEMORY INTERNAL TO THE TOOL

RELATIONSHIP TO EARLIER FILED APPLICATION

This application claims priority under 35 U.S.C. Sec. 119 to U.S. Prov. Pat. App. No. 61/050,430, filed 5 May 2008, the contents of which are explicitly incorporated herein by reference.

FIELD OF THE INVENTION

This invention is generally related to a surgical tool system that includes a surgical tool with a power generating unit and a console, the console able to read data in a memory integral with the tool over the conductors over which power is sourced to the tool.

BACKGROUND OF THE INVENTION

The ability to perform modern surgical procedures is facilitated in part by the development of instruments, sometimes referred to as tools, able to shape, remove or transform tissue. Electrosurgical tools are one such class of instruments. An electrosurgical tool system includes both a tool and a control console. The tool system includes at least two electrodes. The console sources a current between the electrodes. Some electrosurgical tools are monopolar tools. This type of tool includes a structural device designed for application to tissue that includes at least one electrode. This electrode is considered the active electrode. When this type of tool is employed, the system includes a ground pad. The ground pad is placed against the body of the patient to function as the return electrode. Other electrosurgical tools include structural devices designed for application to tissue that include at least two electrically disconnected electrodes. This type of tool is generally referred to as a bipolar tool. When a bipolar tool is in use, one or more electrodes function as the active electrode. The remaining one or more electrodes function as the return electrode.

When an electrosurgical tool is employed, current is flowed from the active electrode(s) through the target tissue to the return electrode(s). The internal resistance of the tissue converts the electrical energy to thermal energy that heats the tissue. The heating of the tissue causes the tissue to undergo a state change that is therapeutically advantageous. Some electrosurgical tools, such as forceps and loop pencils are used to cut or coagulate tissue to which they are applied. The coagulation stops blood loss from the tissue. Other electrosurgical tools are in the form of probes. Some probes are designed to ablate the tissue to which they are applied. One such class of probes ablates nerve cells that transmit chronic pain signals to the brain. Other electrosurgical tools remove relatively large sections of tissue to accomplish other therapeutic effects.

An electrosurgical tool system includes more than the tool. The system also includes a control console and a cable. The console includes a power signal generator. The power signal generator outputs an AC power signal at a potential often above 100 Volts to the electrosurgical tool. A control module integral with the console regulates the power signal generator to allow characteristics of the power signal applied to the tool to be varied. Tool power signal characteristics that can be varied include: voltage; current; signal frequency; pulse duty cycle; pulse envelop; and pulse repetition frequency. The characteristics of the power signal applied to a tool vary with tool type, the type of procedure and preferences of the individual practitioner.

The cable includes conductors over which the power signal is applied to the tool.

Often, an electrosurgical tool and its complementary control console are provided as a single system. This is because a particular tool is typically designed to receive power signals that have a specific set of characteristics. It is common practice to design the console so the console can only source power signals that can be applied to the tool with which the console is to be used. The practitioner is able to vary characteristics of the power signal within a specific range appropriate for that tool. A disadvantage of these systems is that should a medical facility use plural different tools with very different power requirements, the facility is obligated to provide plural control consoles that differ only in the characteristics of the power signals they source.

A remedy to this arrangement is to provide a control console able to source energization signals over a wide range of output characteristics. Such a system could rely on the operator to manually set the characteristics of the sourced power signal. If an individual is allowed to so set the characteristics of the power signal, the console could inadvertently be configured to source a power signal that is inappropriate for the tool to which the signal is applied. Such configuration of the system could result in the console sourcing a power signal that causes the tool to malfunction. A more serious result of such misconfiguration is that the system applies a current to the patient that inadvertently causes tissue damage.

A solution to the above problem is to provide a NOVRAM in the surgical tool and a complementary assembly in the console to read the tool NOVRAM. The NOVRAM, a non-volatile memory, stores data that describe the characteristics of the power signal that should be sourced to the tool. The console processing circuit reads these data. Based on these data, the processing circuit ensures that the power supply components internal to the console only source power to the tool that have appropriate characteristics for the tool. The Applicants' Assignee's U.S. Pat. No. 6,017,354 and its Application U.S. Pub. No US 2007/0016185 A1, both of which are incorporated herein by reference, disclose how it is possible to provide an electrosurgical tool system with such components.

Configuring an electrosurgical tool system automatically based on data in a memory integral with the tool facilitates rapid system set-up. Limiting the extent to which a tool power signal can be adjusted based on the data in the tool memory reduces the likelihood human error can result in an incorrect system set-up. Nevertheless, there are some limitations with known systems. This type of system requires a cable with conductors to supply power to the tool electrode/electrodes and additional conductors over which signals are read from the tool memory. The need to provide the cable with these multiple conductors makes it more expensive to provide than a conventional two-wire, power signal only, cable. Requiring use of such a cable makes it difficult to use the control console with tools not equipped with internal memories. A medical facility would like a console to have this utility so the console is also able to energize different types of tools, even tools without memories. However, if the console is configured to power both types of tools, different cables would be required. A first cable is required for tools that have memories. A second cable is required for tools without memories. This requires the facility to keep both types of cables available for use. Further, when configuring the system, personnel must take the time to ensure that the attached cable is appropriate for the tool being used.

The above-described tool with memory assembly is itself of limited utility. This is because, as described above, use of the tool requires use of the special cable with at least one conductor solely for sourcing power and at least one conductor solely for facilitating the reading of the data from the tool memory. This type of cable could not therefore be connected to a conventional console that source power to conventional, memoryless, tools. Accordingly, if one were to provide the above-described tool, use of the tool would be limited to the consoles specifically designed to receive the cable designed for use with this tool.

Also, there are procedures when it is desirable to, with the same tool, power signals having different characteristics to the same section of tissue. Specifically there are times when it is desirable to first cut tissue and then coagulate the cut tissue. The signal used to cut tissue is typically in the form of a continuous AC waveform. The electrical energy contained in the tissue quickly vaporizes the water internal to the cells of the tissue so that the cells burst. The cell bursting is the cutting of the tissue.

As soon as the tissue is cut, it is often desirable to apply a second signal to coagulate the tissue; stop the blood loss. A coagulation signal may have the same maximum peak-to-peak voltage as a cut signal. However, the coagulation signal is typically not applied as a continuous signal. Instead when the system is in the coagulation mode, the signal applied to the tool is typically in an on-off-on-off pulse form. Each pulse may consist of a number of cycles of the AC power signal. Sometimes each cycle of a pulse has the same peak-to-peak voltage. Sometimes the initial cycle/cycles of a signal pulse have a first, relatively high peak-to-peak voltage; the remaining cycles have peak to peak voltages that decay from the peak-to-peak voltage of the initial cycle/cycles. The coagulation power signal is not a continuous power signal to limit the current flowed through the tissue. The limiting of tissue current flow reduces the extent to which the current flow heats the tissue. Consequently, instead of the current generating heat that causes cell destruction, only enough heat is generated to cause fluid, blood, coagulation.

Stated another way, the crest factor, the ratio of peak voltage to the rms voltage, for a coagulation power signal is typically greater than the crest factor for a cut power signal.

It is a relatively simple task to provide a monopolar surgical tool with on tool switches that allow the practitioner to select which type of power signal is sourced to the tool. However, to date, it has proved difficult to provide a bipolar tool with the same type of on-tool control. When a practitioner wants to use such a tool to sequentially apply different currents to a tissue, means other than an on-tool switch are used to set the current type. Sometimes, for example, a practitioner must rely on another individual to manually actuate a control member integral with the console. Each time the practitioner wants to switch current states for the tool he/she must: give a verbal command; wait for the assistant to hear the command; wait for the assistant to actuate the appropriate switch; and then wait for the assistant to inform the practitioner the command was acted upon. Having to take all these steps, can appreciably increase the time it takes for the tool current settings to be switched. Given the length of these time gaps, some practitioners find bipolar electrosurgical tools unsuitable for performing procedures for which such tools are otherwise well designed.

Further, there are times when a practitioner wants to provide irrigation fluid when using an electrosurgical tool. Both monopolar and bipolar electrosurgical tools that include conduits through which irrigation fluid is pumped to the site the tool is applied are known. However, to date, it has proved difficult to provide a tool, especially a bipolar tool that allows the practitioner to, with one hand, both position the tool at the site and control both tool activation and whether or not irrigation fluid is discharged at the site.

SUMMARY OF THE INVENTION

This invention relates to a new and useful surgical tool system. The system of this invention includes a console, a tool and a cable for connecting the tool to the console. The tool includes a component designed for application to a surgical site that performs its therapeutic or diagnostic effect when power signals are supplied to the tool. Integral with the tool of this invention is a memory. The memory stores data for configuring the console for operation with the tool. The memory is connected to circuitry internal to the tool by the conductors over which the power signal is sourced to the tool electrode/electrodes. Also internal to the tool is an isolation circuit. When signals are sent from the console to the tool memory to read data from the memory, the isolation circuit applies these signals to the tool memory without appreciably changing their characteristics. That is, without changing the characteristics of these signals to the point at which the tool memory is not able to respond to the signals. When, power signals are applied to the tool, the isolation circuit substantially changes the characteristics of the nature of the signals that are applied to the memory. That is the isolation circuit changes these signals so that the changed signals, when applied to the tool memory, do not adversely affecting the tool memory.

The console includes an assembly for reading data from the memory. This assembly retrieves data using signals that have characteristics different from the power signals applied to the tool electrode/electrodes. The console includes a isolation circuit that substantially eliminates if not prevents the power signals sourced to the tool from being applied to the memory reader assembly.

The system of this invention provides a means to supply power signals to powered surgical tools including electrosurgical tools and read the data in the memory internal to the tool over a single pair of wires.

Some versions of the tool of this invention have multiple memories. Each memory stores data identifying a different tool operating state. Switches on the tool allow the practitioner to select which of the memories is selectively read. Based on which memory is read, the console applies one from a number of different number or power signals to the tool to place the tool in a specific one of a number of different operating modes. Alternatively, based on which memory is read, the console either sources power to the tool, causes an irrigation fluid to be pumped through the tool to the surgical site; or simultaneously sources power while causing the irrigation fluid to be pumped. The practitioner can, with the same hand that holds the tool, depress the switch that places the tool in one of the above different operating states.

BRIEF DESCRIPTION OF THE DRAWINGS

The invention is pointed out with particularity in the claims. The above and further features, advantages and benefits of the invention are better understood by reference to the following Detailed Description taken in conjunction with the accompanying drawings in which:

FIGS. 15A and 15B, when assembled together, form a block and diagrammatic view of another alternative tool of this invention.

DETAILED DESCRIPTION

I. System Overview

Figure 1:
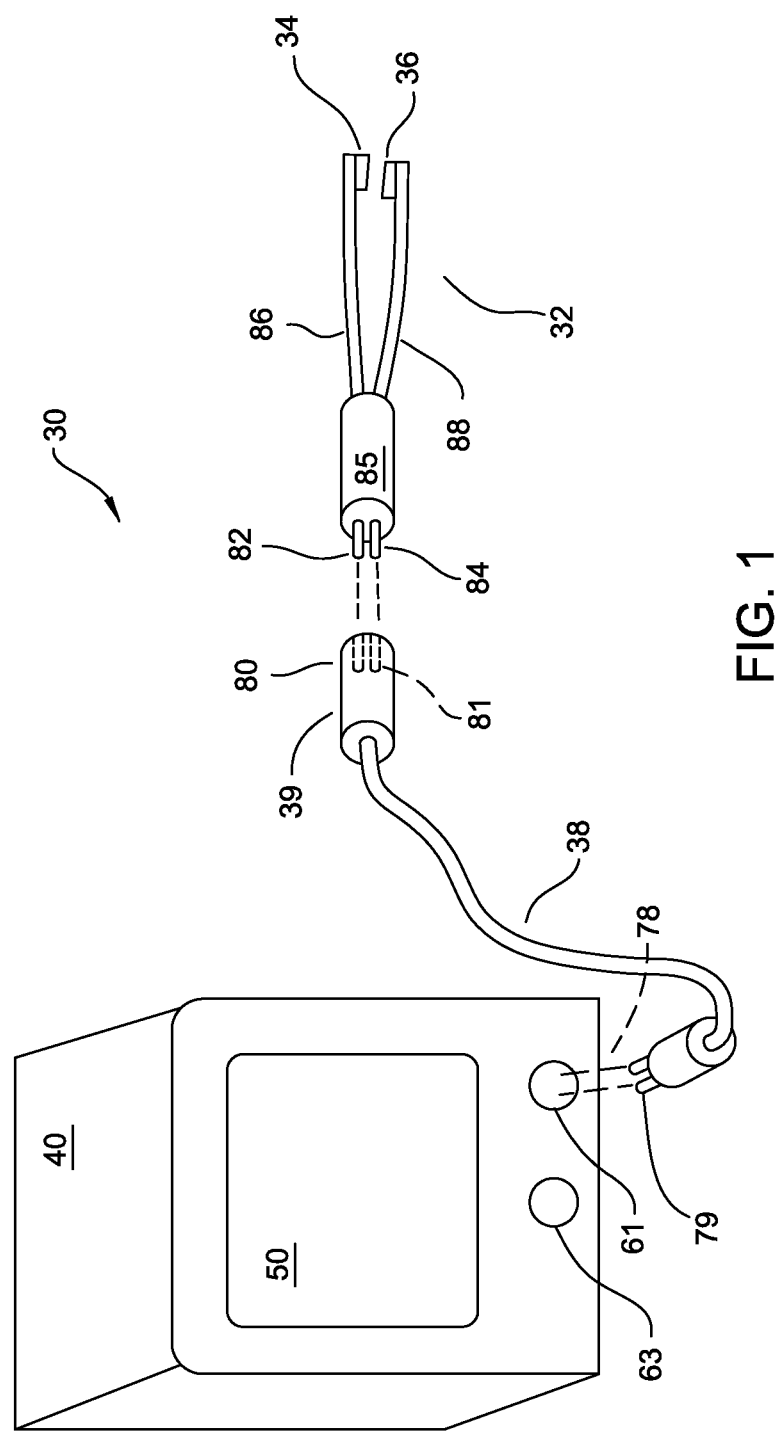
FIG. 1 depicts the components of an electrosurgical tool system of this invention.

A surgical tool system 30, specifically an electrosurgical tool system, of this invention is initially described by reference to FIG. 1. System 30 includes an electrosurgical tool 32. Tool 32 of FIG. 1 is a pair of forceps. This type of tool is a bipolar tool in that the opposed surfaces at the ends of the tool tines 86 and 88 are formed to function as opposed electrodes 34 and 36, respectively. System 30 includes a console 40 that sources power to the tool 32. The power signal is sourced through a cable 38 that extends between the console 40 and the tool 32.

Figure 2:
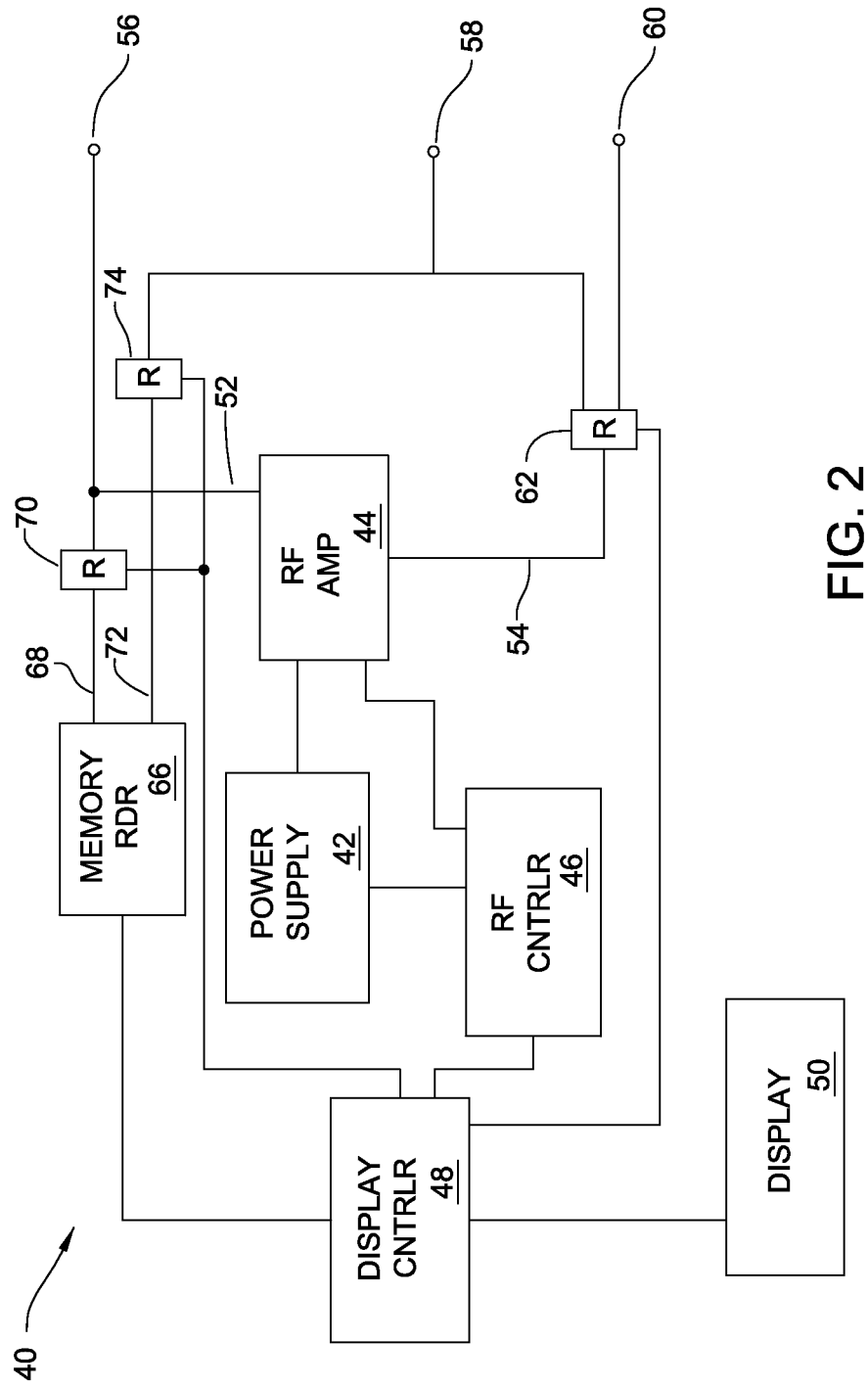
FIG. 2 is a block diagram of the components internal to the console of the system.
Figure 7:
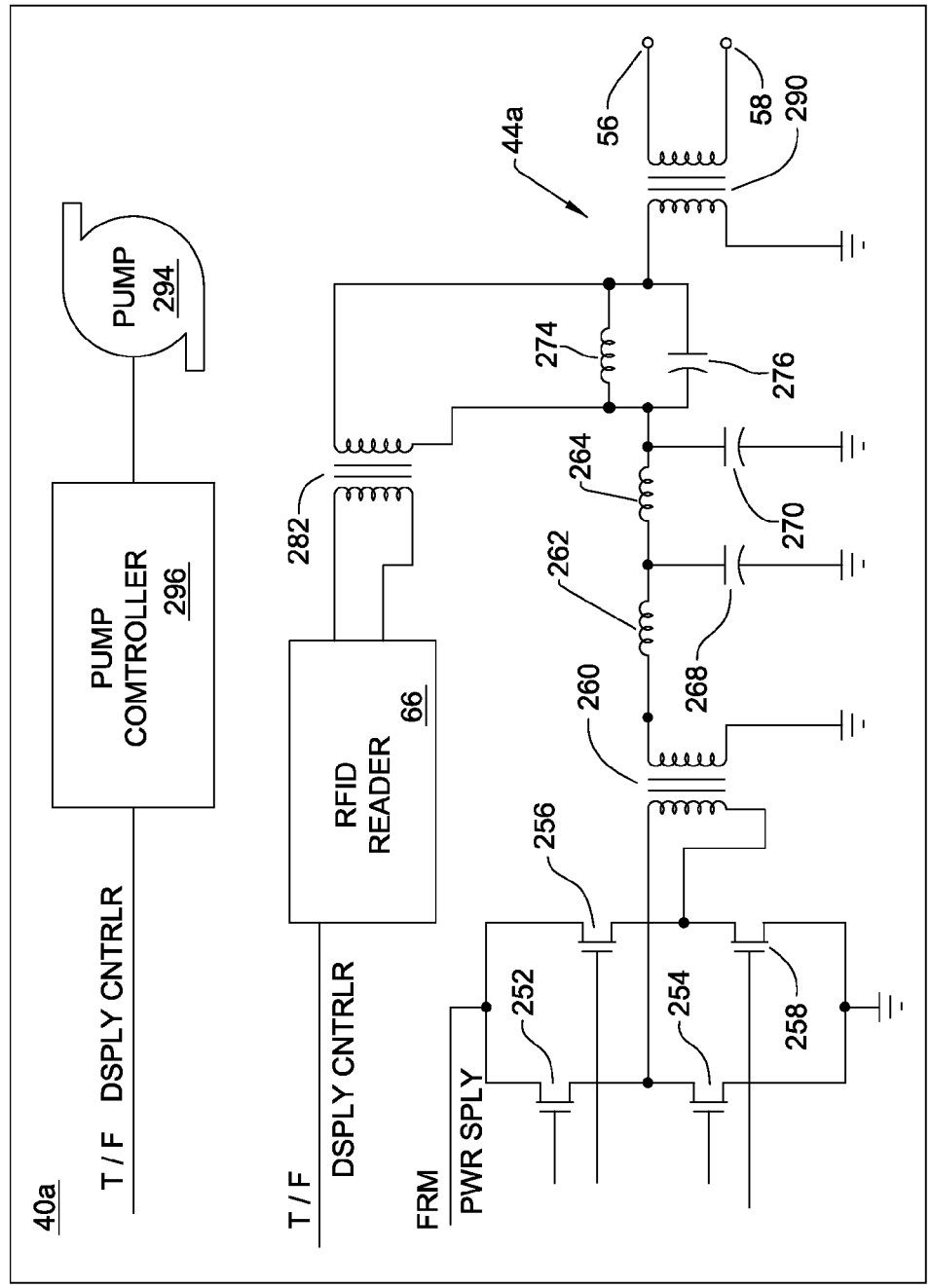
FIG. 7 is a schematic and diagrammatic view of an alternative control console constructed in accordance with this invention.

Console 40, as seen in FIG. 2, includes a power supply 42 and an RF amplifier 44. Power supply 42 outputs a constant DC voltage to the RF amplifier 44. RF amplifier 44 converts the signal from the power supply 42 into an AC power signal that is applied across the tool electrodes 34 and 36. In one version of the invention, RF amplifier 44 consists of an H-bridge and a series of inductors, capacitors and a transformer. The H-bridge is formed by two pairs of series-connected FETs. An exemplary circuit of an RF amplifier is seen in FIG. 7.

An RF controller 46 asserts the signals to the RF amplifier 44 to regulate operation of the amplifier. More particularly, the RF controller 46 asserts signals to the gates of H-bridge FETs. The RF controller 46 is also connected to the power supply 42 for regulating the level of the DC signal supplied by the power supply. Collectively, these control signals are asserted to regulate the characteristics of the power signal sourced by the console 40 to the tool 32. The characteristics of the signal that are set include: voltage; frequency; duty cycle; pulse envelop; and pulse repetition frequency. A digital signal processor can function as the RF controller 46.

A display controller 48, also internal to the console 40, provides overall control of the system 30. Display controller 48 also generates data regarding the operation of system 30. These data may be presented on the display 50, also part of console 40. In some versions of the invention, display 50 is a touch screen display that presents images of buttons for depression by the practitioner. Display controller 48 can be a processor such as the GDPXA255A0C300 processor from the Intel Corporation of Santa Clara, Calif. One set of inputs display controller 48 is from the practitioner. These inputs may be provided through the depression of button images presented on the display 50, the setting of control knobs or switches on the console 40 or the depression of pedals integral with a foot controller (console knobs, console switches and foot controller not shown). While not called out as a separate component, it should be understood that internal to and/or attached to the display controller 48 are one or more memories. These memories are where instructions for regulating operation of console 40 are stored.

Based upon the inputs received, display controller 48 generates instruction signals to the RF controller 46. Based on these instructions, RF controller 46, regulates operation of power supply 42 and RF amplifier 44. This results in the RF amplifier 44 sourcing power signals to the tool 32 that have the appropriate characteristics. The power signals sourced by RF amplifier 44 are output over, arbitrarily, active and return conductors 52 and 54, respectively.

The RF signals to the tool are asserted to the tool over two of three terminals 56, 58, and 60. Terminal 56 and 58 are the terminals in the console socket 61 (FIG. 1) to which cable 38 is connected. Terminal 56 represents the terminal to which a connection to the tool is always established independent of whether the tool is a monopolar or bipolar tool. Active conductor 52 is connected to terminal 56. Thus, terminal 56 can be considered the terminal through which the RF amplifier is connected to the tool "active" electrode. If the tool is a bipolar tool, as is tool 32, the "return" electrode is integral with the tool. When this type of tool, the connection from the cable to terminal 58 connects the return electrode through return conductor 54 to the RF amplifier 44.

A monopolar tool can be used with console 40. In this configuration of system 30, the return electrode is a ground pad 230 (FIG. 6), also part of the system. The RF amplifier 44 is connected to this electrode through terminal 60. Terminal 60 is within a socket 63 on the console 40 to which the ground pad 230 is connected. A relay 62 selectively connects the return conductor 54 that extends to the RF amplifier 44 to terminal 58 or terminal 60. The state of relay 62 is controlled by a signal asserted by the display controller 48. In some versions of the invention relay 62 is a tri-state relay. In these versions of the invention in the normal state relay 62 does not connect return conductor 54 to either terminal 58 or terminal 60

Also internal to the console 40 is a memory reader 66. Memory reader 66 is capable of reading data from or writing data to a memory 90 (FIG. 3) internal to the tool 32. In one version of the invention, memory reader 66 is capable of sending and receiving pulsed AC signals. In some versions of the invention, the memory reader is a Radio Frequency Identification Device (RFID) reader that transmits/receives signals at a frequency of approximately 13.56 MHz. One potential RFID reader that can be integrated into control console 40 is the SLRC41TOFED available from NXP Semiconductor of the Netherlands.

Memory reader 66 exchanges signals with the tool memory 90 through the console terminals 56 and 58. One conductor, conductor 68 in the drawings, extends from the memory reader 66 and is connected active conductor 52 and, by extension, terminal 56 through a relay 70. A second conductor, conductor 72, also extends from the memory reader 66 for exchanging signals with the tool memory 90. Conductor 72 is selectively connected to terminal 58 by relay 74. The open/closed states of relays 70 and 74 are controlled by signals asserted by display controller 48.

Memory reader 66 is connected to the display controller 48 for exchanging data signals. Display controller 48 also regulates the actuation of the memory reader 66, when the reader reads data from or writes data to the tool memory 90.

Figure 3:
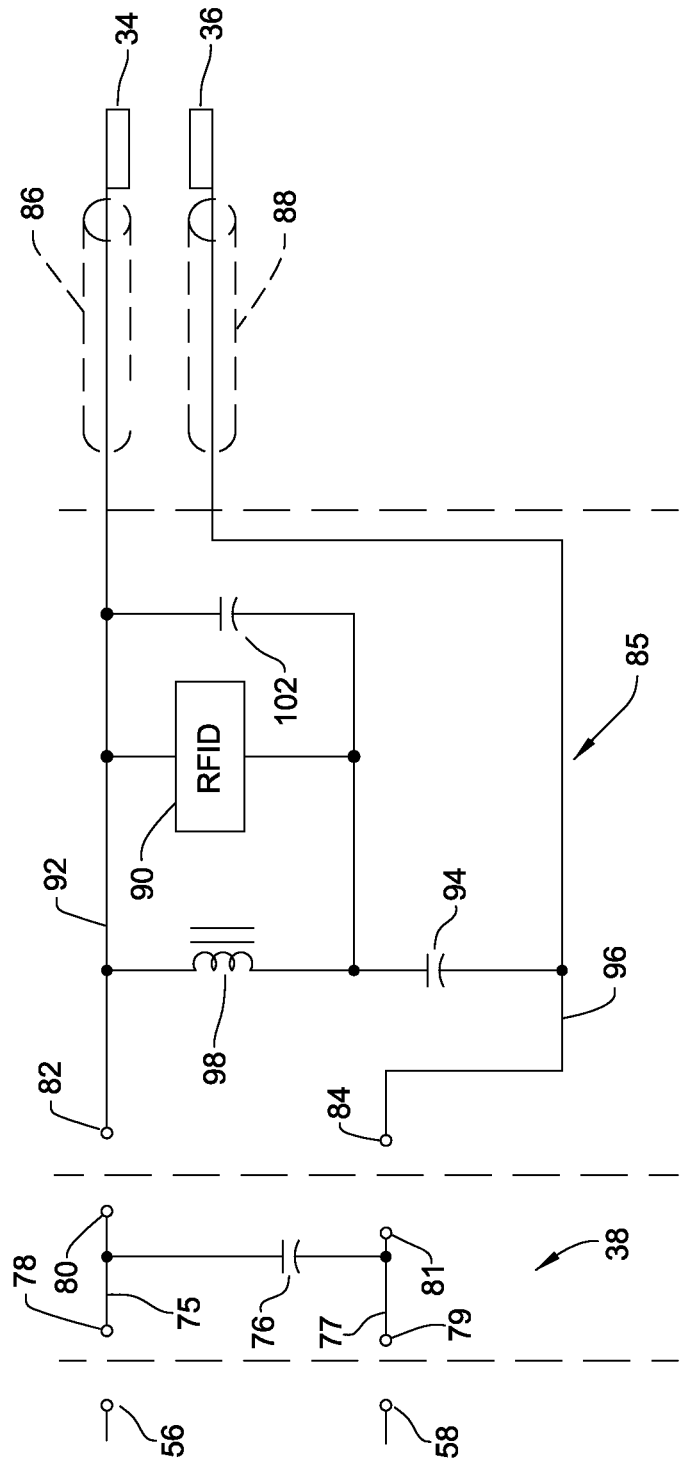
FIG. 3 is a schematic diagram of the components integral with a bipolar tool of this system and the cable used to connect the tool to the console.

The electrically active components of the bipolar electrosurgical tool 32 and cable 38 are now described by reference to FIG. 3. Cable 38 includes two electrically insulated conductors 75 and 77. As with any pair of closely bound conductors, there is an inherent capacitance between conductors 75 and 77. For reasons apparent below, the capacitance between conductors 75 and 77 is represented in FIG. 3 by capacitor 76. Cable 38 also has at its proximal end two pins 78 and 79. Pins 78 and 79 connect to console terminals 56 and 58, respectively, to establish a releasable connection between the cable 38 and the console 40. At the distal end of the cable there is a plug 39 (FIG. 1). Internal to plug 39 are two sockets 80 and 81, (sockets in phantom). Sockets 80 and 81 receive pins 82 and 84, respectively, of the tool 32 to establish an electrical connection between the tool and the cable 38. Typically, cable 38 is connected to both tool 32 and the console 40 without the presence of supplemental fastening components.

Mechanically it should be understood the tool 32 includes a hub 85. Connector pins 82 and 84 are mounted to and extend proximally from the hub 85. Each pin 82 and 84 is dimensioned to be removably seated in a separate one of the sockets 80 and 81, respectively, at the distal end of the cable 38. Two tines 86 and 88 extend from the opposite end of the tool hub 85. The proximal ends of the tines 86 and 88, the ends adjacent hub 85, are pivotally attached to hub 85 so that the tines can be selectively pivoted towards each other. One electrode, arbitrarily electrode 34, is disposed on the inner face of tine 86 adjacent the distal end of the tine. The second electrode, electrode 36, is disposed over the distal end of the second tine, tine 88. Tines 86 and 88 are constructed so that electrodes 34 and 36 face each other. In FIG. 3, tines 86 and 88 are shown as phantom cylinders.

Disposed inside tool hub 85 is tool memory 90. Memory 90 exchanges signals with memory interface 66 internal to the console 40. In some versions of the invention an RFID tag, such as the SL1IC3001, also available from NXP Semiconductor, functions as tool memory 90. Tool memory 90 has two complementary inputs (not identified) across which AC signals are applied in order to write data to and read data out of the memory. One of the inputs to tool memory 90 is connected to a conductor 92 internal to the tool hub 85. Conductor 92 extends from pin 82 through tine 86 to electrode 34. The second input to tool memory 90 is connected to hub pin 84 by a conductor 96. Conductor 96 also serves as the conductor internal to tine 88 over which power signals are sourced to tool electrode 36. The second input to tool memory 90 is connected to conductor 96 through a capacitor 94. Not identified is the conductor that extends from the input of memory 90 to capacitor 94.

Also internal to the tool hub 85 is an inductor 98. Inductor 98 is connected across memory 90 such that one end is connected to conductor 92 and the second end connected to the junction of the input to memory 90 and capacitor 94. Internal to tool memory 90 is a capacitor. In FIG. 3, this capacitor is depicted as a distinct capacitor 102 connected between conductor 92 and the junction of memory 90 and capacitor 94.

Capacitor 94 is selected so that, at frequencies essentially at the maximum frequency of the power signal sourced by RF amplifier 44, the capacitor has a high impedance, at least 5000 Ohms. In some versions of the invention, capacitor 94 has a capacitance of 15 pF or less.

Collectively, inductor 98 and memory capacitor 102 form a tank circuit. In some versions of the invention, inductor 98 is selected so that the inductor and capacitor 102 form a tank circuit that has a resonant frequency slightly offset from the frequency at which memory reader 66 and tool memory 90 are configured to exchange signals. This design selection is due to the means by which data are read from the tool memory 90. Specifically, memory reader 66 outputs an interrogation signal at a specific frequency. Tool memory 90 transmits data back to the reader 66 by modifying the impedance of the circuit comprising the memory 90, inductor 98 and capacitor 102. This modification occurs by the selective toggling of a resistor or capacitor internal to the memory (internal switched resistor/capacitor not illustrated). The change in impedance changes the percent of power of the interrogation signal consumed by the tool memory 90. Memory reader 66 monitors the consumption of energy by memory 90. The memory reader interprets changes of power consumption by the tool memory circuit as distinct data pulses.

The circuit over which the interrogation signal is output contains more components than the tool memory 90, inductor 98 and the capacitor 102 internal to the memory. This circuit also includes hub capacitor 94 and the capacitance of the cable conductors 75 an 77, capacitor 76.

Figure 4:
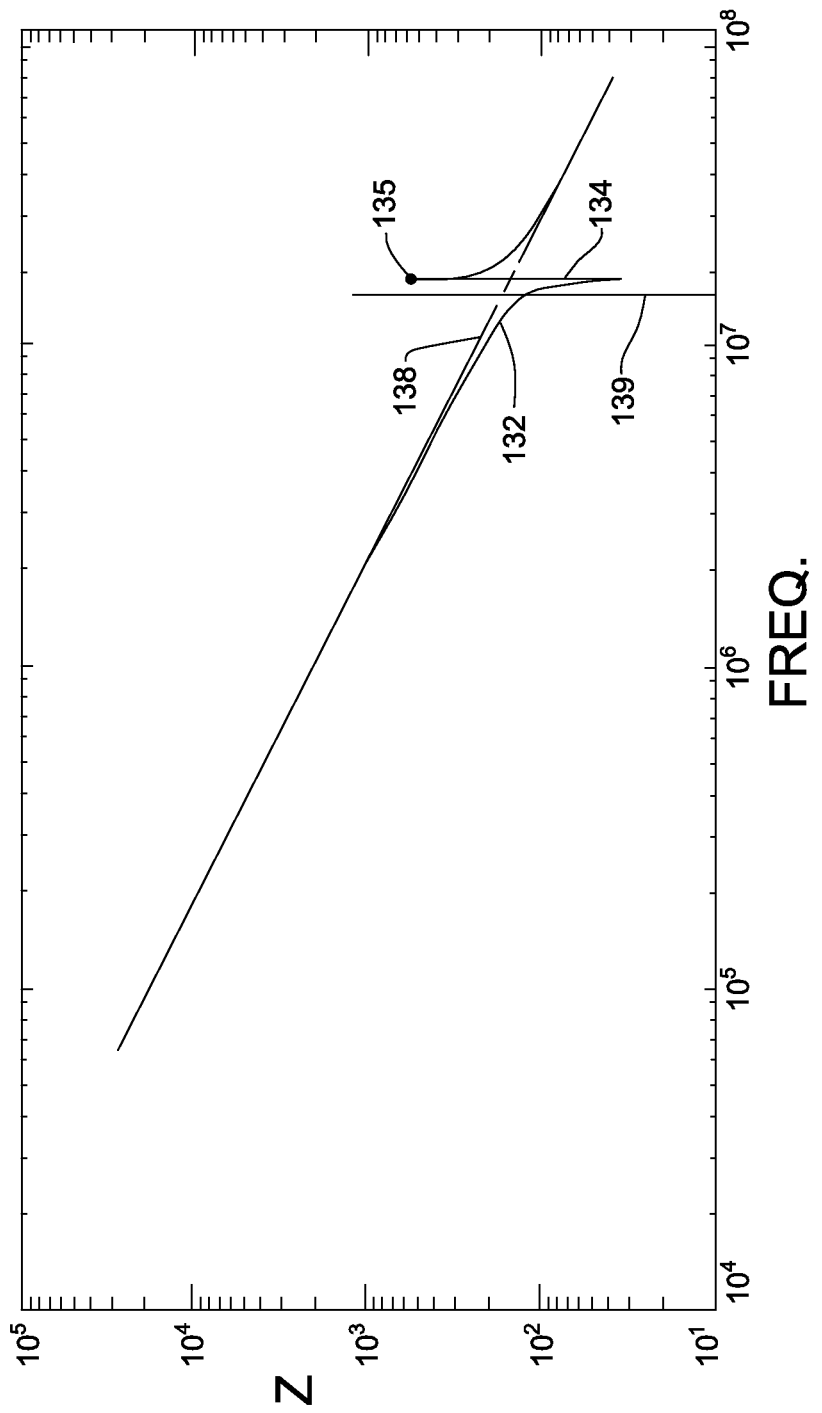
FIG. 4 is a diagram depicting the relationship between signal frequency and circuit impedance for memory circuit internal to a tool of this invention.

FIG. 4 represents the frequency-impedance plots for the tool memory circuit. Two plots are shown. Plot 132, represented by a solid line, represents the impedance when the resistance internal to the tool memory is relatively high. In many memories, this is the state when the data signal is turned on; the tool memory circuit impedance can be, for example, approximately 20,000 Ohms. When the circuit is in this state, the resonant frequency of the plot is represented by the essentially vertical plot segment 134. Point 135, essentially the high impedance terminal point of plot segment 134, represents the point at which the circuit has its high impedance resonant frequency.

Plot 138, represented by a dashed line segment, represents the frequency/impedance plot when the resistance internal to the tool memory 90 is relatively low, for the given example, approximately 200 Ohms. Tool memory 90 is in this state when the data signal is off. In contrast to when the high resistance setting results in the impedance profile having first a low spike and than a high spike, the impedance profile of plot 138 is substantially linear.

As described above, memory reader 66 determines the on/off state of the tool memory signal based on the power consumed by the tool memory circuit. This power is a function of circuit impedence.

A potential problem could arise if the circuit is configured to have a resonant frequency equal to the frequency of the interrogation signal. This problem is due to the fact that, while cable capacitance (the capacitance of capacitor 76) can be estimated, it can vary from cable to cable. The variation in cable capacitance means that the resonant frequency of the circuit can be slightly more than the frequency of the interrogation signal. In this situation, the interrogation signal can be at the frequency that intersects or comes very close to the point where segment 134 of signal plot 132 crosses plot 138, the data off impedance signal. In this situation, the power consumed by the tool memory circuit would not significantly vary from when the memory is in the data on and data off states. Memory reader 66 would therefore not be able to detect the changes in power consumption that otherwise normally accompanies the data on/off toggling of the memory 90.

To reduce the likelihood of the memory circuit data on/data off impedance levels approaching at which the difference is undetectable, inductor 98 is selected so that the tool memory circuit has a resonant frequency offset from the frequency of the interrogation signal applied to the tool memory 90. The offset should be such that interrogation frequency fails within the spectrum of frequencies for which the differences in impedances between the data on and data off circuit states are readily detectable. In FIG. 4, line 139 represents the abscissa at the interrogation frequency. It is seen that this line intersects the data in and data off impedance plots 132 and 138 at two widely spaced apart points. If, due to variations in the cable capacitance, the impedance plots 132 and 138 shift to the right or left a small amount, line 139 still will intersect plots 132 and 138 at two widely spaced apart points. Therefore, even if the plots shift, the changes in memory circuit impedance due to the data on/data off toggling are still detectable.

In one version of constructing this invention, inductor 98 is selected to have an inductance, $L_{REAL}$, that is approximately 1.4 $L_{IDEAL}$ where $L_{IDEAL}$ is the inductance the inductor should have so that the tool memory circuit has a high impedance resonance frequency equal to the tool memory interrogation frequency.

II. System Operation

Figure 5A:
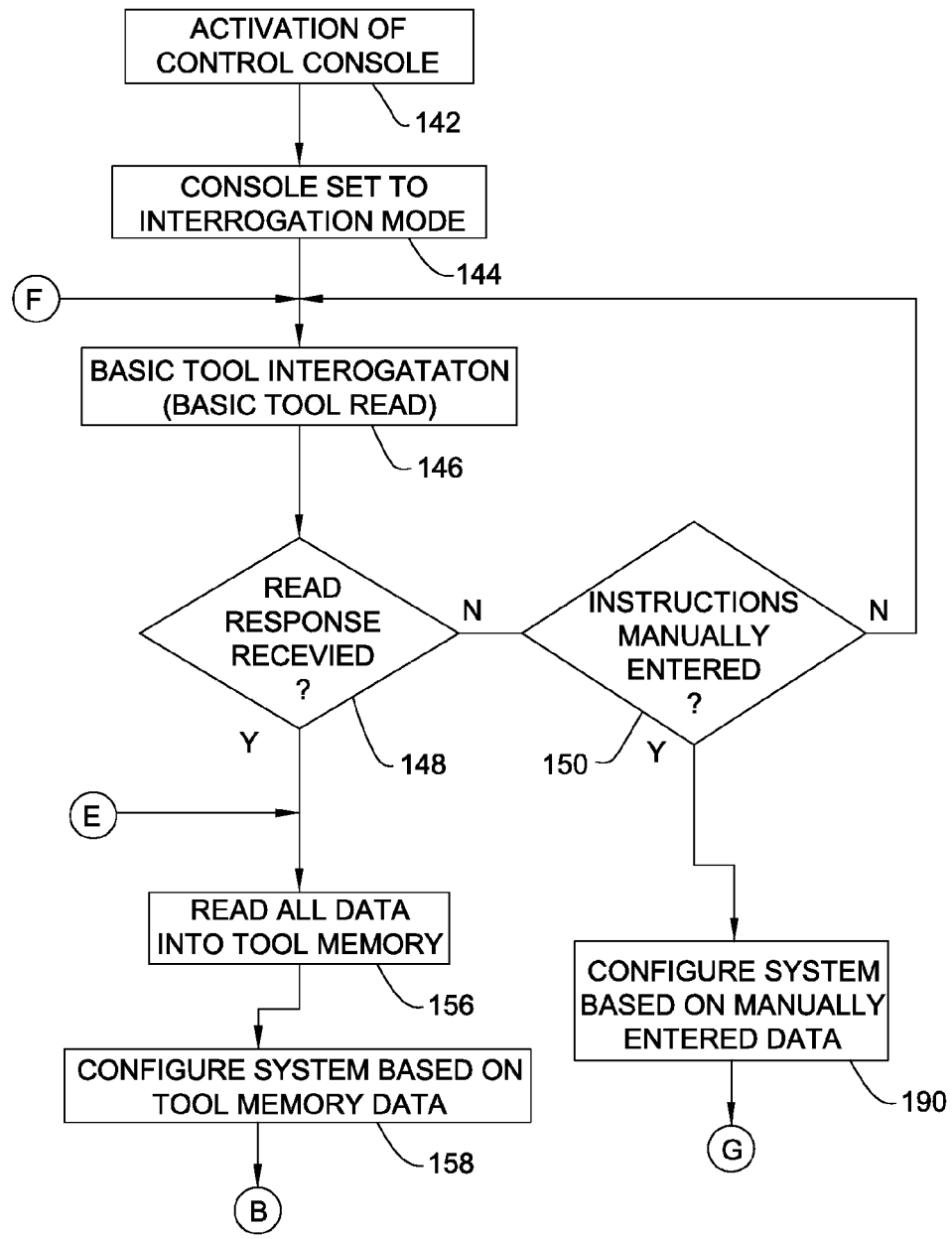
FIGS. 5A through 5C, when assembled together, form a flow chart of the process steps executed by the system of this invention to configure the system upon attachment of a tool and subsequently energize the tool.
Figure 5B:
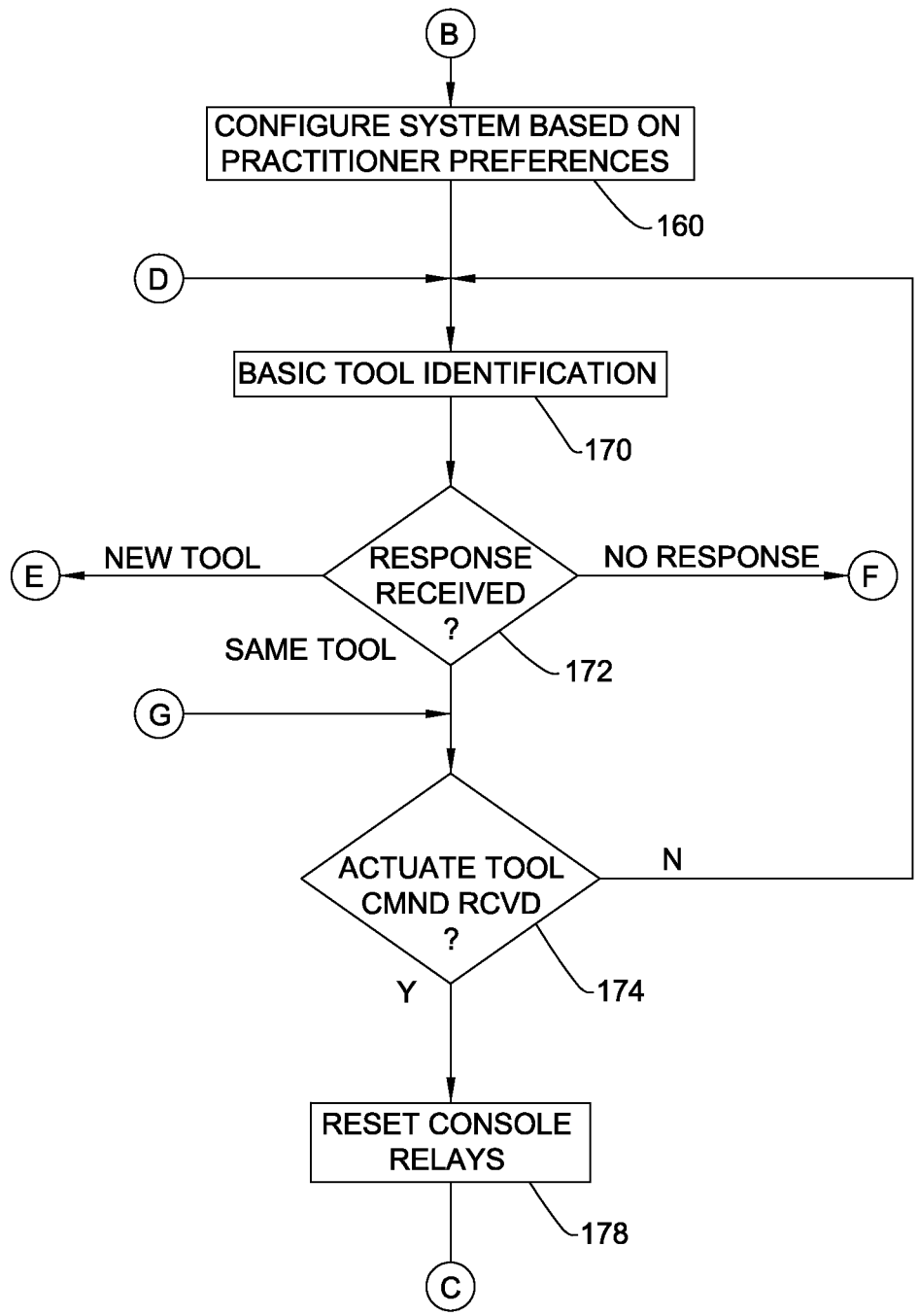
Figure 5C:
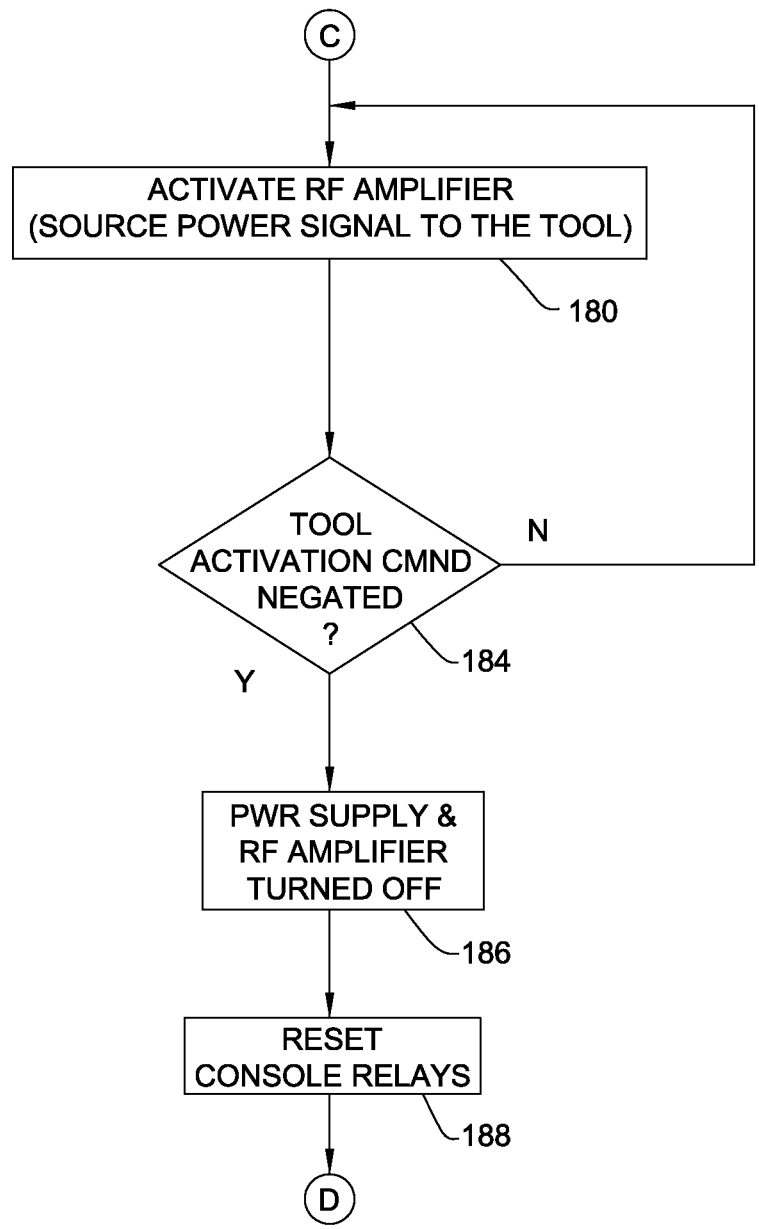

The process by which system 30 of this invention sources a current from one electrode 34 or 36 through the tissue to a second electrode 36 or 34 is now described by reference to FIGS. 5A through 5C. Step 142 represents the activation of control console 40. Integral with the activation of the control console 40 are self-tests the console performs. The activation of the console 40 and self-tests are performed by the display controller 48 based on pre-loaded instructions.

At the completion of the actuation and self-test of the control console 40, display controller 48 places the console in an interrogation mode, step 144. As part of the process of entering the interrogation mode, during the execution of step 142, display controller 48 sets relays 70 and 74 to tie memory reader 66 to console terminals 56 and 58.

Once in the interrogation mode, display controller 48 periodically instructs memory reader 66 to perform a basic interrogation, step 146. In the basic interrogation step 146, memory reader 66 outputs a basic read command over cable conductors 75 and 77. This read command, as well as all other read/write signal transmissions exchanged between the control console 40 and the tool, is transmitted at low voltage, typically 10 V or less and is transmitted for less than 1 ms.

When the read command is transmitted, system 30 may be in one of three potential states. In a first state, there is either no cable 38 connected to the console 40 or no tool connected to the cable.

In a second state, a tool that does not contain a memory is connected to the cable 38. In this state, the application of the signal across cable conductors 78 and 79 results in a current flow between the electrodes of the tool (or between the electrode of the tool and the complementary ground pad.) However, given the low potential of this signal and the high impedance of the tissue between the electrodes (or the electrode and the ground pad,) there is essentially no current flow through the tissue. Thus the transmission of the read command signals cannot be considered the transmission of signals that result in the actuation of the tool that results in tissue changes.

When system 30 is in either of the above two states, since there is no memory present, there is no response to the read command, test step 148. Step 150 represents the detection by the display controller 48 of manually entered commands. Step 150 occurs in this operational state of system 30 when a tool without a memory is attached to cable 38.

Display controller 48 interprets the absence of a response to the read command of interrogation step 146 or the absence any manual setting of the console that a tool is not connected to console 40. If system 30 is in this state, the display controller 48 continues to periodically execute basic interrogation step 146 and wait for a response to this interrogation, step 148, or an indication the system is being manually configured, step 150.

A tool 32 with a memory 90 may be connected to cable 38 (connection step not shown). When system 30 is in this state and basic interrogation step 146 is executed, the AC signal comprising a basic read command is applied to the tool hub tank circuit with which the memory 90 is integral. In response to receipt of this read command, memory 90 transmits a reply, writes basic data out, to the memory reader (step not shown). These data, as well as the other data read out from memory 90, are read out over the isolation circuit, connector pins 82 and 84, cable power conductors 75 and 77 and tool relays 70, 74 to the console memory reader 66.

In this basic reading of the tool memory data, the control console 40 reads the data that identifies the type of tool and data that identifies the tool with specificity. These latter data are a serial number unique to the tool. Other data potentially read out in this step potentially include an authorization code and data indicating the number of uses to which the tool has been subjected.

As part of the transmission of the read command to the tool memory 90 and the reading of data out, the signals forming these commands and data transmissions are applied to capacitor 94. The circuit comprising memory 90, capacitor 94, inductor 98 and capacitor 102 can be considered to be an isolation circuit. The components forming this isolation circuit are, as described above, selected such that, when the interrogation signal is applied the circuit and data are transmitted out through the circuit, the circuit is near resonance. There is a minimal voltage drop and power loss through capacitor 94. This voltage drop across and power loss in the isolation circuit does not appreciably change the characteristics of the signals applied to or received from tool memory 90. Here, an "appreciable" change in the characteristics of the signal applied to the tool memory 90, or back to the console memory reader 66 would be a change that results in the application of a signal to the tool memory or console that the memory or console was unable to process. In the described embodiment of the invention, the isolation circuit may cause a small drop in potential of the interrogation signal, or the signal written out from the memory, relative to the potential of the signal applied to terminals 82 and 84 and conductors 92 and 96. However, the voltage drop is not appreciable enough to prevent the tool memory 90 or console memory reader 66 from processing the applied signals. In this version of the invention, an appreciably changed signal applied to the tool memory 90, is a signal that has a potential of 80% or less of the potential of the interrogation signal (or written out data signal) applied to terminals 82 and 84.

Console memory reader 66 forwards the data read out from tool memory 90 to display controller 48. These data are then stored in the appropriate memory integral with or attached to the displace controller 48. These sub-steps as well as the other sub-steps of the transfer of data from the memory reader 66 to the display controller 48 are not shown. Display controller 48, in step 148, interprets the receipt of these basic tool identification data as an indication that a tool 32 with integral memory 90 is attached to the cable 38; the result of the test of step 148 is positive. If system 30 is in this state, display controller 48, instructs memory reader 66 to read all the data in the tool memory 90, step 156. Step 156 also represents the reading out of the data in the tool memory 90 to the console reader 66 and the forwarding of these data to the display controller 48.

In step 158, display controller 48 performs an initial configuration of the system 30. This system configuration is based on the data retrieved from the tool memory 90. In step 158, the ranges of characteristics at which the system are to operate for the particular attached tool are established based on the data read from the tool memory. These characteristics include: the frequency or range of frequencies at which the power signal should be applied; the voltage or range of voltages at which the power signal should be output; and minimum and maximum currents for the signal. For a signal that is applied as a set of discrete pulses, the characteristics include the pulse repetition frequency, pulse envelop and/or the pulse duty cycle.

Whether or not in step 158, the display controller configures the system to a specific operating parameter or a range of parameters is a function of both the parameter and the tool 32. For example, a particular tool may be designed to receive power signals at a specific frequency. For that tool, the display controller 48, based on the configuration data sets the console to only output power signals at the frequency specified in the tool memory. The frequency range data from the tool memory 90 are employed in the below described practitioner-set configuration step 160.

Also as part of step 158, display controller 48 may establish default settings for some of the characteristics of the power signal. These default settings may be based on data read for the tool memory 90. Alternatively, practitioner-defined signal characteristics may have been previously loaded in the display controller memory. In this situation, once the practitioner is identified to the display controller 48, as part of step 156, display controller 48 retrieves the appropriate practitioner-established characteristics. Display controller 48 then uses these characteristics as the basis for configuring the system 30.

Step 160 represents the practitioner-set configuration of the system 30. In step 160 the practitioner configures the system operating characteristics that can be set within a range for the specific procedure based on the specific procedure to be performed and his/her preferences. These operating characteristics are defined by the practitioner entering the characteristics through the appropriate I/O device such as the touch screen display 50.

In step 160, the practitioner may attempt to enter a setting for the power signal for the attached tool that is outside the range of the settings based on the data in the tool memory 90. Depending on the signal characteristic and the tool, the display controller 48 may prohibit the setting of the characteristic outside of the range. Alternatively, in response to this attempt to set an operating characteristic to an out of range value, the display console 48 may present an out of range notice it requires the practitioner to acknowledge. Once the practitioner acknowledges this notice, the display controller 48 allows the out of range setting of the operating characteristic to proceed.

Once step 160 is executed, system 30 is configured for operation based on the operating parameters defined by the tool memory 90 and the preferences of the practitioner.

Display controller 48 then cyclically repeats a basic tool identification step 170, a receive response step 172 and an actuate tool command received step 174. Basic tool identification step 170 is analogous to basic interrogation step 140. Display controller 48, through the memory reader 68, issues a read command requesting the tool memory provide the serial number for the tool. In receive response step 172, display controller 48 reacts to the response to this read command. A response that contains the same serial number as originally received is interpreted as indicating the same tool 32 remains attached to the console 40. A response with a different tool serial number is interpreted as an indication that a new tool is coupled to the console 40. In this situation, display controller 48 loops back to step 156 so as to cause all the data in the tool memory 90 to be read out and forwarded to the processor 48. Steps 158 and 160 are reexecuted based on the operating characteristics data for the new tool.

Alternatively, there may not be a response from the tool to the basic interrogation step 170. Display controller 48, in step 172, interprets this no-response received event as indicating that the previous tool was disconnected from the console and that there is either no new tool or a tool without a memory attached. The display controller 48, upon making this determination, loops back to cycling through the basic interrogation step 146, the basic response received step 148 and the manual configuration command received step 150.

More typically, in receive response step 172 the response is the same serial number as originally received in step 148. Accordingly, the display controller 48 awaits receipt of an actuate tool command, step 174. Until such a command is received, steps 170, 172 and 174 are continually reexecuted.

The actuate tool command may be entered through a user-actuated control member, the exact structure of which is not relevant to this invention. For example, the command may be entered in response to the depression of the image of a tool actuate button presented on display 50. As described below, the response may be entered by the practitioner depressing a switch on the tool 32. Alternatively, the command may be entered by the depression of the pedal on the footswitch assembly connected to the console 40.

The initial response to the receipt of an actuate tool command is, in step 178, the setting of the console relays 62, 70 and 74. If the tool memory 90 data indicates the tool is bipolar tool, relay 62 is set to connect return conductor 54 to terminal 58. If the tool memory data indicates the tool is monopolar tool, display controller 48 sets relay 62 to connect the return conductor to terminal 60. Display controller 48 also resets relays 70 and 74 to disconnect the memory reader 66 from the conductors 52 and 54.

Once the relays 62, 70 and 74 are set, the display controller 48 instructs the RF controller 46 to turn on both the power supply 42 and the RF amplifier 44. More specifically, RF controller 48 directs the power supply 42 to output a DC signal at the appropriate voltage level. Simultaneously with the output of the DC signal, RF amplifier 44 is actuated by the RF controller 46 so that the RF amplifier outputs a tool power signal as specified by the defined output signal output characteristics. Collectively, these sub processes are represented in FIG. 5C by step 180.

The power signal applied over the cable conductors 75 and 77 to the tool hub 85. At the relatively low frequency of the power signal, under 1 MHz, inductor 98 acts as a low impedance bypass round the tool memory 90. Capacitor 94 appears as a high impedance load between hub conductors 92 and 96. Thus, when the power signal is applied, the isolation circuit formed by capacitor 94, inductor 98 and capacitor 102 substantially changes the characteristics of the signal applied to the tool memory. Here a "substantial" change in the signal is a change to the signal that affects the signal to such an extent that, when the changed signal is applied to the tool memory 90, the changed signal does not adversely affect the memory. In the circuit of FIG. 3, isolation circuit affects this change by substantially reducing the portion of the potential of the signal across terminals 82 and 84 applied to tool memory 90. Here, a substantial change in the characteristics of the signal is reduction in the potential of the power signal applied to the tool memory 90 to a level at which the signal does not adversely effect the memory. In other words, only a small fraction of the power of the power signal is applied to the tool memory 90. The relatively low potential of this signal, typically, 2 V or less in the described version of the invention, means that the signal does not adversely affect the memory 90. Generally, the substantially changed potential is one that is reduced by at least 20% relative to the power signal potential across the terminals 82 and 84. Often, the substantially changed potential of the signal applied to the tool memory 90 through the isolation circuit is 50% or less of the potential of the signal across the terminals 82 and 84.

The major fraction of the power contained in the power signal is, instead, applied through conductors 92 and 96 to tool electrodes 34 and 36, respectively. The resultant current flow between the tool electrodes 34 and 36 results in the heating of the tissue between the electrodes and the desired end effect caused by such heating.

Console 40 outputs the activation signal to the tool 32 until the actuation command is negated, step 184. Upon the negation of actuation command, display controller 48, in step 186, instructs the RF controller 46 to turn off both the DC power supply 42 and the RF amplifier 44. The turning off of the DC power supply 42 and the RF amplifier 44 causes the outputting of the power signal to cease.

Once the outputting of the RF energization signal ceases, display controller 48 in a step 188, resets the console relays, step 188. Relay 62 is reset to the open state. Relays 70 and 74 are reset to reconnect the memory reader 66 to terminals 56 and 58, respectively.

Upon the resetting of the console relays, display controller 48 returns to the process of the cyclic reexcution of steps 170, 172 and 174. When the tool is be reactivated, steps 180-186 are reexcuted.

As described above, there may be times when a tool without a memory is attached through cable 38 to the console 40. When system 30 is so configured, the practitioner configures the system for operation based on the intended electrosurgical current for that tool. This task is performed by the actuation of the control members associated with the console 40. The display controller 48, in step 150, recognizes the depression of the control members as the manual configuration of the console 40. In response to receipt of these commands, in step 190, the display controller appropriately configures the power generator and the RF controller.

Once step 190 is executed, the system 30 is ready for use. Display controller 48 proceeds to step 174 to await receipt of an activate tool command. Once the practitioner actuates a control member to actuate the tool, the system proceeds through the previously recited steps of: setting the relays 70 and 74 to disconnect the memory reader 66 from conductors 52 and 54; the setting of relay 62 as appropriate; the activation of the RF amplifier to produce the electrosurgical current; and the testing to see if the signal containing the activate tool command has been negated.

Electrosurgical tool system 30 of this invention is constructed to configure the console 40 to output an electrosurgical current based on the power signal characteristics specified in the memory 90 internal to the system tool 32. This automatic configuration of the console 40 occurs faster than it would if the medical personnel were to enter the configuration instructions manually. Since the configuration is automatic, the likelihood human error will cause the console to be incorrectly configured is substantially eliminated.

Another feature of this invention is that the system is configured so that the signals containing the configuration instructions are exchanged over the cable conductors 75 and 76 over which the power signal is applied to the tool. This eliminates the need to provide the cable 38 with additional conductors and the tool and console with additional terminal members for establishing conductive connections to these supplemental conductors.

The above feature of this invention does more than reduce the extent to which adding a memory to the system tool increases the hardware components for a powered surgical tool system. The above feature as well as the structure of the console, makes it possible to use console 40 of this invention with both tools that include memories 90 and conventional, memoryless, tools. Both types of tools can be connected to the console with the same type of cable and are both connected to the same console terminals. The former feature eliminates the need for the facility using system 30 of this invention to have in inventory two types of cables, one for memoryless tools and for tools that contain memories 90. The latter feature means that personnel do not have to exert mental effort to remember to which socket the terminals need to be connected. Also, it should be understood that in many constructions of system 30, cable 38 can be a conventional cable used to connect conventional electrosurgical tools to conventional control consoles.

In sum, system 30 of this invention while designed to facilitate automatic configuration of the console when a tool with a memory 90 is attached, does not impose added burdens when use of a memoryless tool is required.

Still another advantage of the above construction is that a tool 32 of this invention can be used with a console not capable of reading the data in the tool memory 90. Cable 38 can be used to connect the tool to a conventional console. The console is manually set to provide the practitioner-desired power signal to the tool. As when tool 32 is used with console 40, capacitor 94, inductor 98 cooperate to minimize the current applied to the tool memory 90.

III. Monopolar Electrosurgical Tool
(First Alternative Tool)

Figure 6:
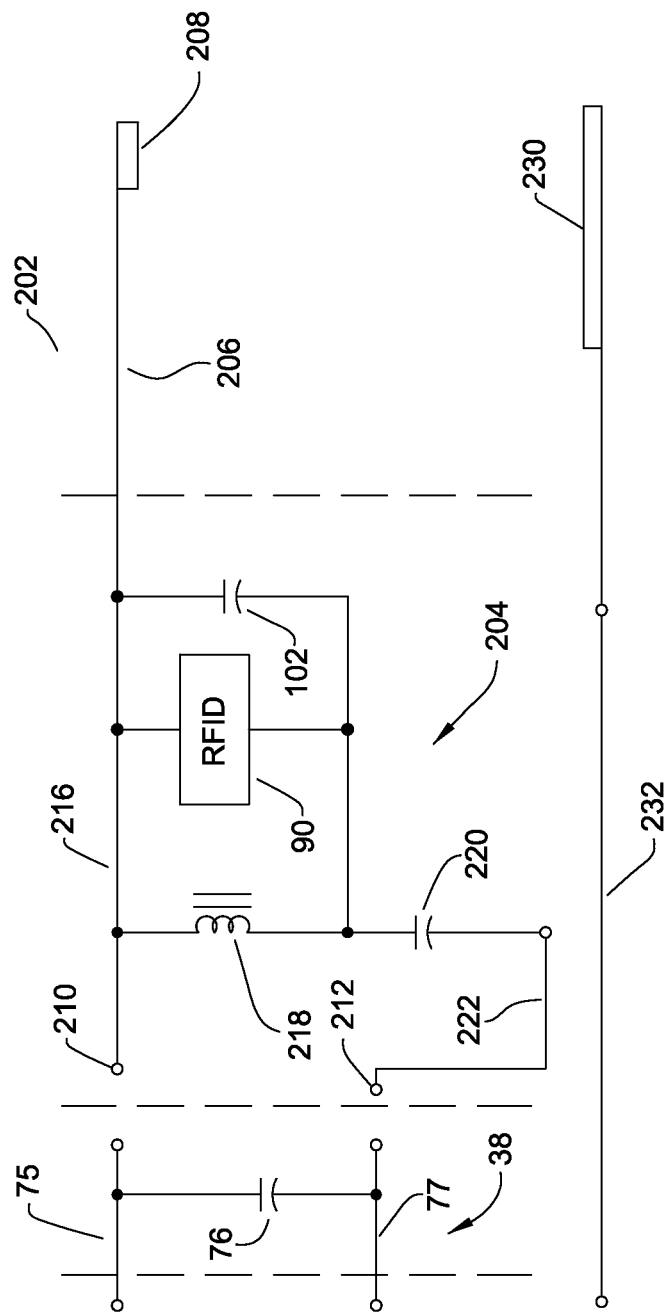
FIG. 6 is a schematic diagram of the components integral with a monopolar tool of this system, the cable used to connect the tool to the console and the associated ground pad.

FIG. 6 is a schematic and diagrammatic view of an alternative electrosurgical tool, a monopolar tool 202 that can be used as part of system 30 of this invention. Tool 202 includes a hub 204 from which a probe 206 extends. A single electrode 208 is disposed at the distal end of the probe 206. Hub 204 includes two pins 210 and 212 for connection to the separate sockets 80 and 81, respectively, internal to cable plug 39.

Tool memory 90, including capacitor 102, is also disposed inside hub 204. A conductor 216 analogous to conductor 92 extends from pin 210 to one of the input pins of tool memory 90. Conductor 216 is also connected to electrode 208. An inductor 218 extends across the data signal inputs of tool memory 90 across which the data signals are applied to the memory. Thus one end of inductor 218 can be considered connected to conductor 216. A capacitor 220 is connected to the opposed end of inductor 218. Accordingly, both the return data signal input of memory 90 and capacitor 102 can be considered connected to the junction of inductor 218 and capacitor 220.

The end of capacitor 220 opposite the end to which inductor 218 is connected is connected to a conductor 222. Conductor 222 is connected to hub pin 212.

Shown diagrammatically in FIG. 6 is a ground pad 230. Ground pad 230 functions as the return electrode for tool 202. A cable 232 connects ground pad 230 to console socket 63.

When monopolar tool 202 is connected to console 40, system 30 of this invention generally operates in the same way it operates when bipolar tool 32 is used. Display controller 48 and memory reader 66 cooperate to read the data in tool memory 90. Based on the read data and the practitioner preferences, display controller 48 configures the console 40 for operation with the tool 202.

The data integral with memory 90 includes data indicating that the tool is a monopolar tool. Accordingly, when an actuation signal is received the result of the test of step 174 is positive, display controller 48 performs a different setting of the relays in step 178. Specifically, relay 62 is, in this execution of step 178, set to establish a connection between return conductor 54 and terminal 60. This setting of relay 62 connects ground pad 230 to the RF amplifier 44. With the establishment of this connection, current can be pulsed between tool electrode 208 and the ground pad 230

Accordingly, a further advantage of system 30 is that based on the data in tool memory 90, the control console 40 configures the system for operation with either a monopolar tool or a bipolar tool. Cable 38, the cable used to connect bipolar tool 34 to the console 40, can also be used to connect monopolar tool 202 to the console.

IV. Alternative Console and Second Alternative Tool

FIG. 7 illustrates some of the sub-assemblies internal to an alternative control console 40a of this invention. Console 40a includes RF amplifier 44a. The RF amplifier 44a includes an H-bridge formed out of four FETs 252, 254, 256 and 258. FETs 252 and 254 are series connected together. FETs 256 and 258 are likewise series connected together. The sources of FETs 252 and 256 are tied together and to the high voltage output line of the power supply 42 (FIG. 2). The drains of FETs 254 and 258 are tied together and to ground.

RF amplifier 44a also includes a transformer 260. One end of a first winding of transformer 260 is tied to the junction of FETs 252 and 254. The second end of the first winding of transformer 260 is tied to the junction of FETs 256 and 258. One end of the second winding of transformer 260 is tied to ground. The second end of the second winding of transformer 260 is tied to two series connected inductors 262 and 264.

A capacitor 268, also part of RF amplifier 44a, is tied between the junction of inductors 262 and 264 and ground. A capacitor 270 is tied between the end of inductor 264 spaced from inductor 262 and ground. The power signal present at the junction of inductor 264 and capacitor 270 is applied to a second transformer 290 through parallel connected inductor 274 and capacitor 276.

One end of the first winding of transformer 290, receives the signal present at the junction of inductor 274 and capacitor 276 spaced from inductor 264. The second end of the first winding of transformer is tied to ground. In FIG. 7, the opposed ends of the second winding of transformer 290 are shown tied to terminals 56 and 58. Not shown in FIG. 7 is how the end of transformer tied to console terminal 58 may alternatively be tied to terminal 60 (FIG. 2).

Console 40a of this version of the invention also includes memory (RFID) reader 66. The opposed terminals of memory reader 66 across which the interrogation signal is applied is connected to the opposed ends of a winding that is part of a transformer 282. The opposed ends of the second winding of transformer 282 are connected to the opposed junctions of inductor 274 and capacitor 276.

Shown diagrammatically in FIG. 7 is a pump 294. Pump 294 can be built into console 40a to supply irrigation fluid. This fluid is pumped to electrosurgical tools 352 (FIG. 13) that, as described, below are formed with conduits through which the fluid is discharged at the body sites to which the tools are applied. In one exemplary version of the invention, pump 294 is a motor that rotates a head. A tube set is positioned against the head. Rollers on the head press against a tube that is part of the tube set. The repetitive action of the rollers forces fluid through the tube set and to the electrosurgical tool. The Applicants' Assignee's U.S. Pat. No. 7,238,010 B2, SURGICAL IRRIGATION PUMP AND TOOL SYSTEM, incorporated herein by reference, provides a more detailed description of the construction of such a pump and complementary tube set.

Pump 294 is regulated by a pump controller 296. Specifically, pump controller 296 regulates the application of the drive signal applied to the motor integral with the pump 294 to both turn the motor on and off and regulate the rate of rotation. Pump controller 296 regulates the drive signal applied to the pump 294 based on control signals received from the display controller 48 (FIG. 2). Typically, the display controller 48 allows the practitioner to control both when the pump 294 is actuated and establish the rate at which fluid is pumped to the tool. Based on these practitioner-entered commands, display controller 48 generates the appropriate instructions to pump controller 296.

Figure 8:
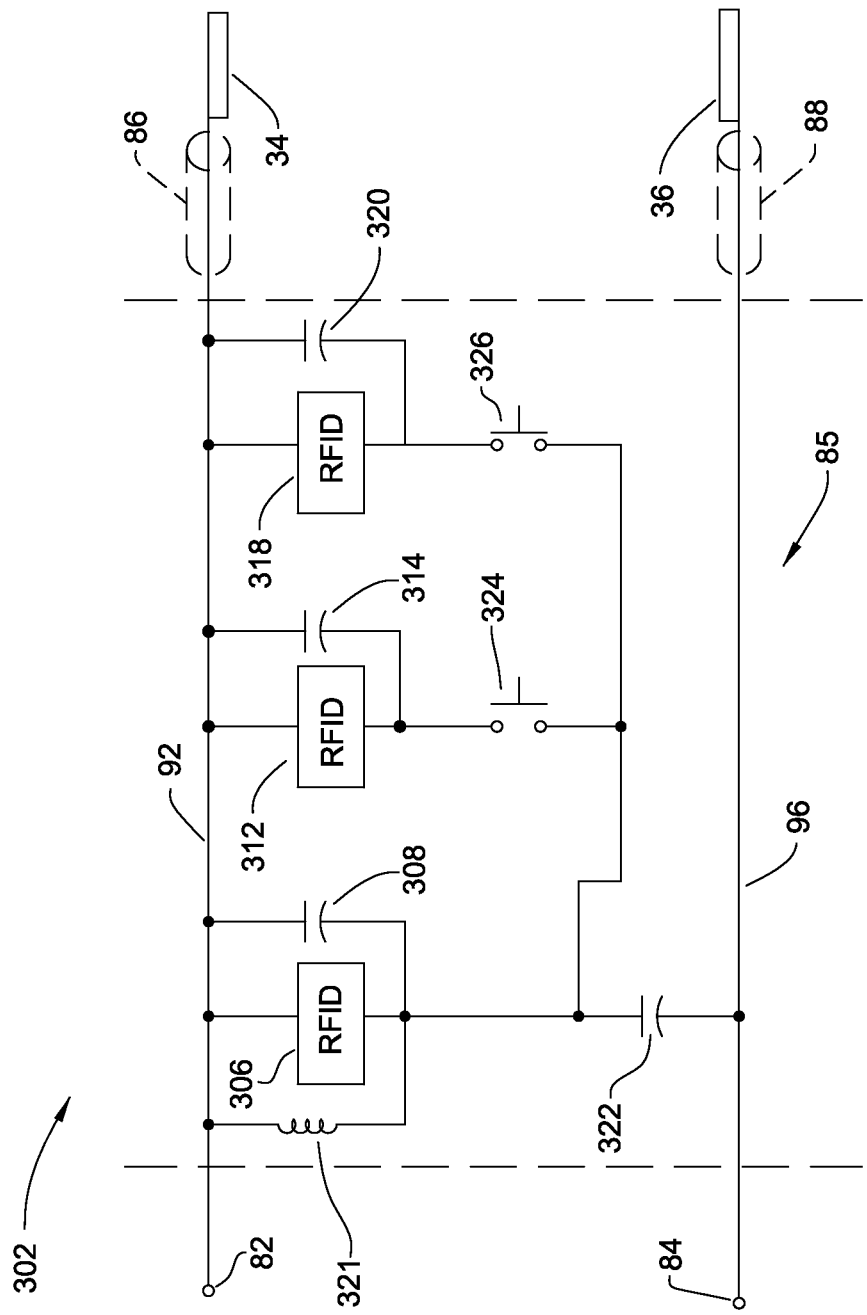
FIG. 8 is a schematic and diagrammatic view of an alternative bipolar tool of this invention that can be used with the control console of FIG. 7.

FIG. 8 illustrates one alternative electrosurgical tool 302 designed for use with console 40a. Tool 302 includes the previously described hub 85, tines 86 and 87 and electrodes 34 and 36. Pins 82 and 84 extend proximally rearward from the hub 85 so that the tool can be connected to console 40a by cable 38. As in the version of the tool described with respect to FIG. 3, conductor 92 connects pin 82 to electrode 34; conductor 96 connects pin 84 to electrode 36.

Internal to hub 85 of tool 302 are three individually addressable memories, (RFID tags,) 306, 312 and 318. The capacitors internal to memories 306, 312 and 318 are represented as capacitors 308, 314 and 320, respectively. Each memory 306, 310 and 318, and the associated capacitor 308, 314 and 320 respectively, are showed having one input connected to hub conductor 92.

An inductor 321 is connected across the opposed input pins of memory 306. A capacitor 322 is connected at one end to the junction of inductor 321 and the second input pin of memory 306. The second end of capacitor 322 is connected to conductor 96. A normally open push button switch 324 is connected between the second input into memory 312 and the junction of inductor 320 and capacitor 322. A second normally open push button switch 326 is connected between the second input into memory 318 and the junction of inductor 320 and capacitor 322. While not illustrated, both switches 324 and 326 may be mounted to the tool hub 85. Alternatively, switches 324 and 326 are mounted to one of the tines 86 or 88. This version of the invention is constructed to allow the practitioner to use the thumb or forefinger to both serve as digit that presses against the tine to close the forceps and that selectively presses either of the switches 324 or 326 closed.

Figure 9:
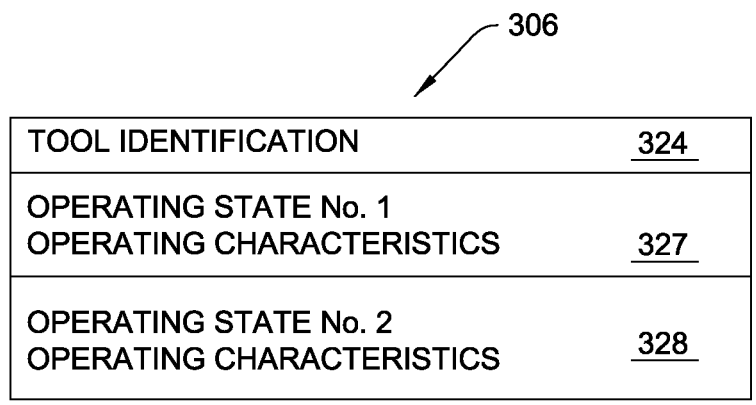
FIG. 9 depicts the data files in the primary memory of the tool of FIG. 8.

FIG. 9 illustrates the data in tool memory 306, which can be considered the primary memory. These data include a tool identification file 324. Tool identification file includes data that both identifies the type of tool and the serial number data that identifies the tool with specificity. Tool memory 306 also includes first and second operating state files 327 and 328. First operating state file 327 contains data describing the characteristics of the power signal sourced to the tool when the tool is in a first operating state, for example the cut state. Second operating state file 328 contains data describing the characteristics of the power signal sourced to the tool when the tool is in a second operating state, for example, the coagulation state.

Figure 10:
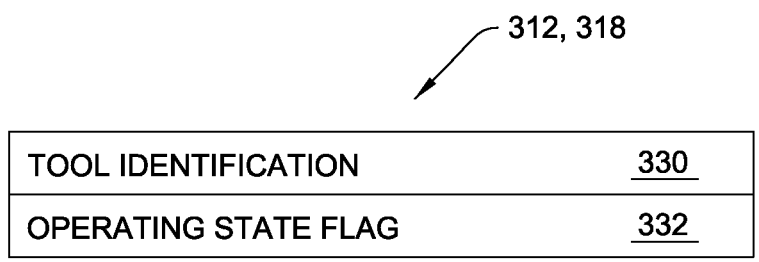
FIG. 10 depicts the data files in the operating state memories of the tool of FIG. 8.

FIG. 10 illustrates the data in tool memories 312 and 318, which are, respectively, the second and third operating state memories. Each tool memory includes a tool identification file 330. Each tool identification file 330 contains the same serial number data for the tool as are stored in file 324 of memory 306. Each tool memory 312 and 318 also contains an operating state file 332. Operating state file 332 contains data indicating in what operating state the tool is to enter. The data in the operating state files 332 for the individual memories 312 and 318 are different. Arbitrarily, memory 312 contains data indicating the tool is be placed in cut mode, memory 318 contains data indicating the tool is be placed in the coagulation mode. Each operating state file 332 may be as small as a single flag bit.

Tool 302 is connected to console 40a by cable 38 (FIG. 1). Once the system is activated, step 142 (FIG. 5A) and basic interrogation step 144 are executed as before. In response to the detection of the presence of the tool, step 148, all data in memory 306 are read in step 156. At least when tool 302 is initially coupled to the system, switches 324 and 326 are open. Owing to that state of these switches, neither memory 312 nor memory 318 receive read requests. Since neither of the memories 312 and 318 receive the read request of step 144, neither of these memories writes out data in response to this request. Further, it should be understood that, using a protocol for reading data from RFID memories, it should be appreciated that the read request of basic interrogation step 144 may include instructions that indicate only memory 306 is to respond to the read request of step 144.

Based on these data received from memory 306, display controller 48, in step 158, configures the system to operate the tool 302 in either the cut or coagulation mode. Step 160 can be executed to allow the practitioner to establish individual preferences for the power signals sourced to the tool 302 when in the cut or coagulation modes.

The previously described basic identification step 170 and response analysis step 172 are performed as with the first described method of operating the system of this invention. In this execution of step 170, memory 306 is instructed to write out the data in the identification file 324 internal to the memory. In this embodiment of the invention the activation of the tool is regulated according to the processes now described with respect to the flow chart of FIG. 11. Specifically, after it is determined that the tool 302 for which the control console 40a is configured remains connected to the console, the execution of step 172, a tool state interrogation, step 338 is executed. In step 338, memory reader 66 sends a command to the tool requesting that any memory other than memory 306 read out its data back to the console 40a.

Depending of the state of switches 324 and 326, there are three potential responses to the read request of step 338. If neither switch 324 nor switch 326 is depressed, there is no response to this read request. Display controller 48, in a step 340, interprets this lack of response as an indication that the practitioner has not actuated the tool 302. Accordingly, the console continues to reexecute steps 170, 172, 338 and 340.

When the practitioner wants to use tool 302 in one of the two modes, the on-tool switch 324 or 326 associated with that mode is actuated. Consequently, when step 338 is executed, the memory 312 or 318 associated with the closed button, reads out the data internal to the memory to the memory reader 66. Memory reader 66 forwards these data to the display controller 48. Initially, as part of the processing of these data, display controller 48 compares the identification data from the file 330 from the memory 312 or 318 to the identification data previously retrieved from memory 306, (step not illustrated). This comparison is performed as a failsafe to verify that the same tool 302 remains connected to the console 40a. If this comparison fails, display controller 48 asserts the appropriate fault notice, (step not illustrated).

Most likely, the above-described comparison will indicate that the data retrieved are from one of the memories 312 or 318 of the initially connected tool 302. Accordingly, in step 340, the display controller 48 interprets the receipt of these data as indication that the tool is to be placed in one of the two operating modes.

In step 342, display controller 48 then generates the appropriate command signals to the power supply 42 and the RF controller 46. The specific commands generated by the display controller 48 are based on the determination of in which mode the practitioner wants the tool to operate. If the practitioner wants the tool to operate in the cut mode, display controller 48 generates commands that result in the console 40a sourcing a continuous power signal. If the practitioner wants the tool to operate in the coagulation mode, display controller 48 generates commands that result in a pulsed power signal being sourced. Whether or not the pulse is a set of signal cycles with a constant peak voltage or one with cycles that decay over the period of the pulse is a function of the state instructions for that particular operating mode. Step 344 represents the actual sourcing of power signals to the tool 302 based on the asserted instructions. The processes that occur in step 344 are similar to the process occurring during the execution of steps 178 and 180.

The power sourced by console 40a is sourced to tool electrodes 34 and 36 over conductors 92 and 96. When the power signal is present across conductors 92 and 96, capacitor 308 functions as a low impedance bypass around memory 306 and the other in circuit memory 312 or 318. The remaining switch 326 or 324 should be open. Current is therefore, not supplied to the memory 318 or 312, respectively, associated with the open switch 326 or 324.

During the sourcing of the power signal, console memory reader continually periodically outputs a tool state interrogation signal, step 346. Step 346 is identical to the above described tool state interrogation step 338. In some versions of the invention, step 346 is executed at least once every 100 millisecond if not at least once every 50 millisecond after power is sourced to the tool.

Step 346 is performed to determine if the practitioner wants the tool to remain active, has switched the operating state of the tool or has turned the tool off. Step 348 represents the processing of the signal returned in response to interrogation step 330. If the practitioner is continuing to using the tool as before, the switch 324 or 326 originally depressed remains depressed. When the tool 302 is in this state, the response to interrogation step 346 will be for display controller 48 to continue to operate the system as prior to the execution of step 348. Accordingly, steps 344, 346 and 348 are continually repeated.

The practitioner stops activating the tool by releasing pressure on the depressed switch 324 and 326. When this event occurs, in response to interrogation step 346, no operating state data are returned to the control console 40a. Display controller 48, in step 348 interprets the absence of returned data as an indication that the tool is to be switch off. Accordingly, as represented by step 349, the display controller 48 negates the assertion of the control signals to the power supply 42 and RF amplifier 44 that cause the sourcing of power. Display controller 48 then returns to the cyclic execution of steps 170, 172, 338 and 340 to await the next indication the tool 302 is to be activated.

In the third alternative, the practitioner may indicate that the tool 302 is to be placed in the second mode of operation, shift from cut to coagulation or from coagulation to cut. The practitioner indicates this switch by shifting which of the two switches 324 or 326 is depressed. When the tool 302 is in this state, in response to the tool state interrogation step 346, operational state data are returned indicating that the tool 302 is to be placed in the other operating mode. In response to receipt of these data, display controller 48, as a result of the analysis of step 348, reconfigures the system. In FIG. 11B this is represented by display controller 48 now asserting to the power supply 42 and the RF controller 48 instruction signals that cause the power signals for the new mode of operating to be sourced, step 350.

Display controller 48 then returns to execute steps 344, 346 and 348 to both source the required power signal to the tool 302 and monitor the open/closed states of switches 324 and 326.

During use of the above-described version of the system of this invention, it is apparent that there are times when the power signal and the data read and response signal are simultaneously present across console terminals 56 and 58. Inductor 274, capacitor 276 and transformer 28 function as an isolation circuit between RFID reader 66 and console terminals 56 and 58. This isolation circuit allows the exchange of interrogation signals and the response signals from the tool memories 306, 312, 318 without appreciably changing the characteristics of these signals. Here an "appreciable" change in the characteristics of the signals is a drop in potential of the interrogation signals that are applied to the tool memory, relative to their potential at terminals 82, 84 such that they can not be processed by the tool memory. A similar appreciable change is the drop in potential of the data signals written out of the tool memory 90 to a level at which these signals cannot be processed by the RFID reader 66. Likewise this isolation circuit substantially changes the characteristics of the power signals that are applied to the RFID reader 66. Here a substantial change in the power signals is a reduction in the potential of the power signals applied to the RFID reader 66 to a potential low enough so that the portion of the power signal applied to the RFID reader 66 does not adversely affect operation of the memory reader.

There are also therefore times when the power and interrogation signals (or responses to the interrogation signals) are simultaneously present across tool terminals 82 and 84 and tool conductors 92 and 96. Capacitors 308, 314, 320 and 322 and inductor 321 form an isolation circuit internal to tool 302. It is understood that capacitors 314 and 320 are only part of this circuit when, respectively, switches 324 and 326 are closed. This isolation circuit does not cause an appreciable drop in the potential of the interrogation signal applied to terminals 82 and 84 or in the signals output by the memories 306, 312, 318. This isolation circuit does substantially lower the potential of the power signal applied to terminals 82 and 84 that is applied to memories 308, 314 and 318.

During the times when the power signals and interrogation signals (or responses to the interrogation signals) are simultaneously applied to the tool, these signals are both present across tool electrodes 34 and 36. The interrogation and response signals are of relatively low potential, 10 Volts or less. These signals are only present periodically and, when present is present for a period of 1 millisecond or less. Accordingly, the presence of either one of these signals across the electrodes 34 and 36 does not have an appreciable effect on the practitioner-desired current flow in order to accomplish a therapeutic effect or diagnostic goal.

Figure 12:
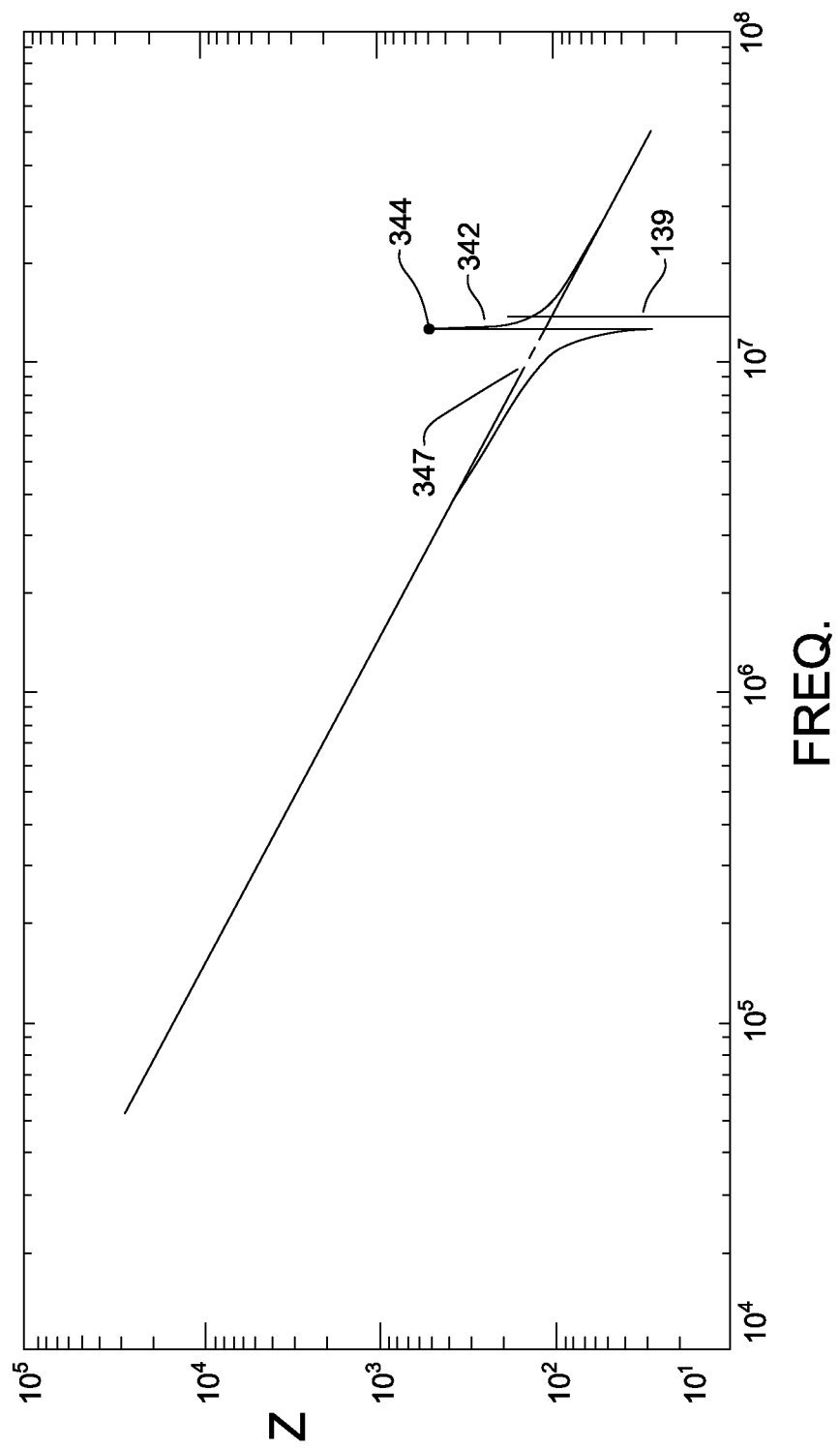
FIG. 12 is a diagram depicting an alternative relationship between signal frequency and circuit impedance for memory circuit internal to a tool of this invention.

Also, it should be understood that the closing of the switch 324 or 326 adds the capacitance of capacitor 314 or 320 to the tank circuit of capacitor 308 and inductor 320. The addition of this capacitance shifts the frequency-impedance plot of cable 38 and tool 302. Specifically, the frequency/impedance plots as represented by point 344 of the high impedance plot 342 of FIG. 12, the high impedance resonant frequency of the circuit when in the high impedance state is less than the frequency when the additional resistor is not connected to the circuit, (the plot of FIG. 4). In FIG. 12, dashed line 347 represents the low impedance plot. As represented by this Figure, it can be seen that the memory interrogation signal, again abscissa line 139, intersects plots 342 and 347 at points where there are detectable differences in circuit impedance between the data on and data off states. Thus, the addition of the added capacitor 314 or 320 does not adversely affect the ability of the memory reader 66 to read data written out of the memories 306, 312 and 318.

When tool 302 is used with the system of this invention, the practitioner, by simple depressing of a switch 324 or 326, places the tool in one of a plural number of operating modes. In response to the depression of the actuated switch, the console 40a determines the mode in which the practitioner wants the tool and sources the power appropriate to that mode. A practitioner, using tool 302 of this invention, can, by simple movement of the finger or thumb, alternatingly apply two different types of current to a surgical site in order to in short order, accomplish two different tasks. Thus, the practitioner can first set the tool to the cut mode in order to cut tissue and then, by the mere alternating of which switch is depressed, set the tool in the coagulate mode in order to minimize blood loss from the cut tissue.

It should likewise be appreciated that, while tool 302 of this invention is designed for single handed mode selection, use of the tool is not limited to this practice. Since tool 302 includes the standard pins 82 and 84, cable 38 can be used to couple the tool to a conventional console for conventional use. When the tool is so used, the practitioner switches operating mode by either depression of particular footswitches or depression of buttons on the conventional console.

V. Tool with Irrigation Conduit (Third Alternative Tool)

Figure 13:
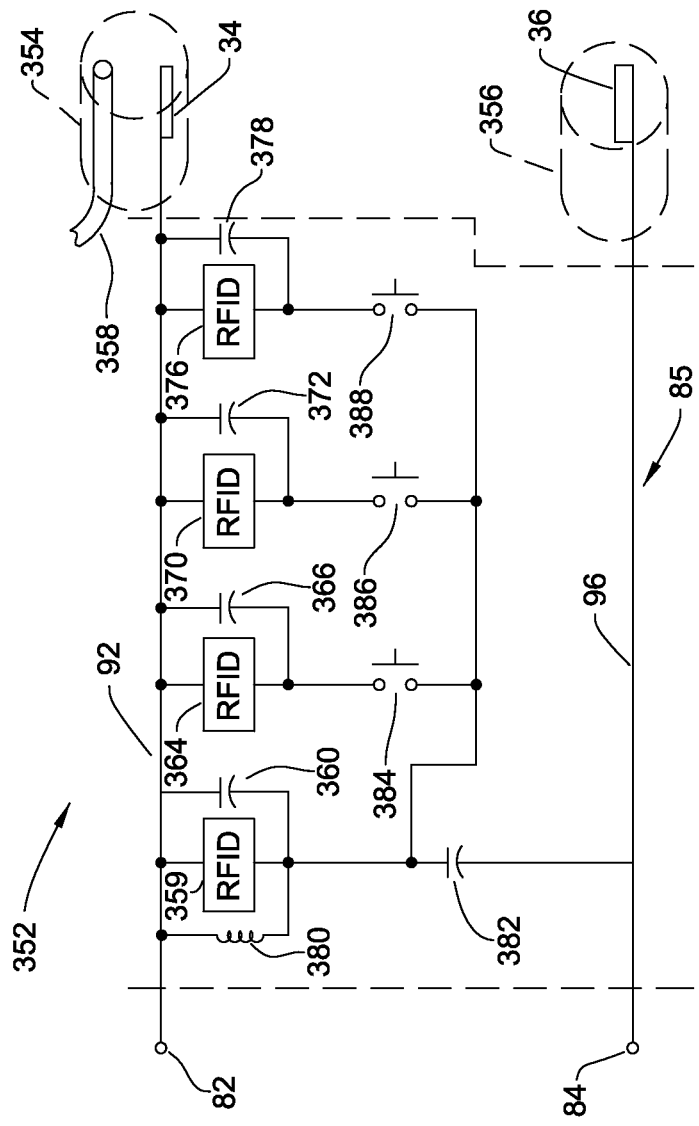
FIG. 13 is a schematic and diagrammatic view of another alternative tool of this invention.

An electrosurgical tool 352 that can be used apply current to tissue and irrigation fluid to a surgical site using the system of this invention is now described by reference to FIG. 13. Tool 352, shown as a forceps, includes the previously described hub 85. Pins 82 and 84 extend proximally from hub 85 for connection to cable 38. Tines 354 and 356, shown as phantom cylinders, extend distally from the hub 85. Electrode 34 is located at the distal end of tine 354. Electrode 36 is located at the distal end of tine 356.

Tine 354 is formed to define an irrigation conduit 358, represented as a tube within the tine. While not shown, it should be appreciated that a fitting may extend proximally rearward from the proximal end of time 354. The fitting is shaped to receive the discharge line from console pump 294. In versions of the invention wherein the irrigation fluid is pumped through a cassette, the discharge line from the cassette is coupled to the inlet fitting. Conduit 358 has an outlet opening, not identified, adjacent the distal end of tine 354. Some electrosurgical tools are designed so that the conduit outlet opening is formed in the surface of the tool on which the electrode is formed.

Internal to hub 85 of tool 352 are the previously described conductors 92 and 96 over which the power signal is sourced to the electrodes 34 and 36. Also disposed inside hub 85 are four memories 359, 364, 370 and 376. Each memory 359, 364, 370 and 376 is tied at one end to conductor 92. Shown in FIG. 13 are the capacitors 360, 366, 372 and 378 connected across the opposed inputs to memories 358, 364, 372 and 376, respectively. An inductor 380 is connected across the opposed inputs of memory 359. A capacitor 382 is connected at one end to the junction of memory 359 and capacitor 360 and inductor 380 that is spaced from conductor 92. The second end of capacitor 382 is connected to conductor 96.

Three normally open push button switches 384, 386 and 388 are also mounted to tool 352. Switch 384 connects the second input of memory 364 to the junction of inductor 380 and capacitor 382. Switch 386 connects the second input of memory 372 to the junction of inductor 380 and capacitor 382. Switch 388 connects the second input of memory 378 to the junction of inductor 380 and capacitor 382.

Memory 359 contains data similar to that contained in memory 306. As represented by the contents of FIG. 9, there are data that identify the tool by both type and specificity. There are data that identify the characteristics of the power signal to be applied to the tool. However, the second operating state file for memory does not contain data indicating the characteristics of secondary power signal that can be sourced to the tool. Instead, second operating state file 328 contains data describing the characteristics of the flow of the irrigation fluid that can be supplied to the tool 352. Often these characteristics are at least partially a function of the diameter of conduit 358. Typically, these characteristics include a range of fluid flow rates. In some versions of the invention, the fluid flow rate data are implicitly represented as a range of rates at which the pump 294 can be cycled.

Memories 364, 370 and 376 contain data similar to the data in tool memories 312 and 318. Each memory 364, 370 and 376 contains the tool identification state file 330 (FIG. 10) with data identifying the tool with specificity. These data are identical for each of memories 364, 370 and 376. Each memory 364, 370 and 376 further contains an operating state file 332 with data identifying a specific tool operating state. Arbitrarily, in one construction of the invention, memory 364 contains data indicating the tool is to be operated in a state wherein only power is sourced to the electrodes 34 and 36. Memory 370 contains data indicating that, simultaneously with the sourcing of power to the electrodes 34 and 36, irrigation fluid is to be supplied. Memory 376 contains data indicating that only irrigation fluid is to be supplied.

Tool 352 is connected to console 40a in the same basic manner as either tool 32 or tool 302. In addition to the connection by cable 38, the discharge line from the pump 294 is connected to the fitting associated with tool conduit 358.

Figure 11A:
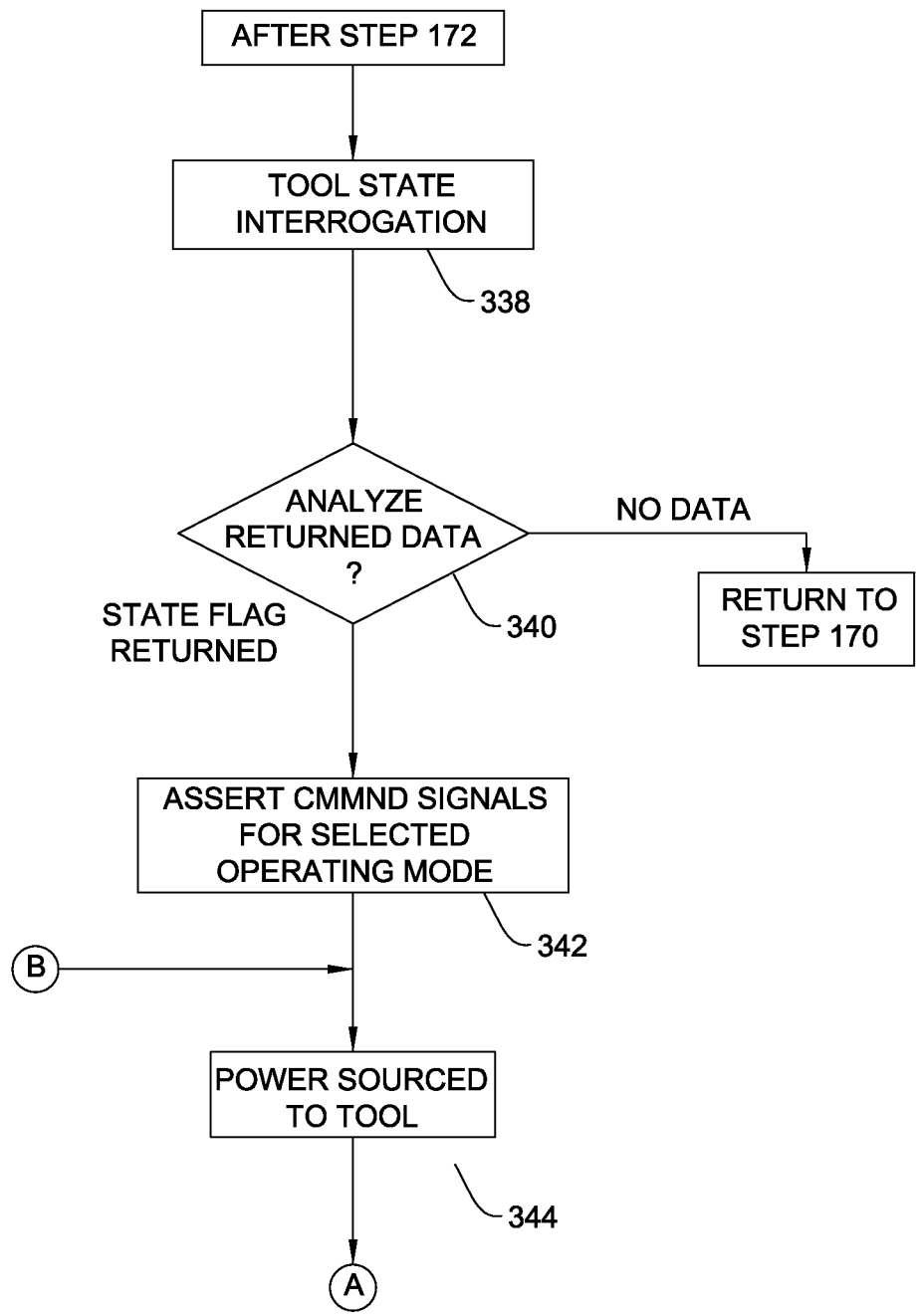
FIGS. 11A and 11B, when assembled together, form a flow chart of the process steps executed as part of the activation of the tool of FIG. 8.
Figure 11B:
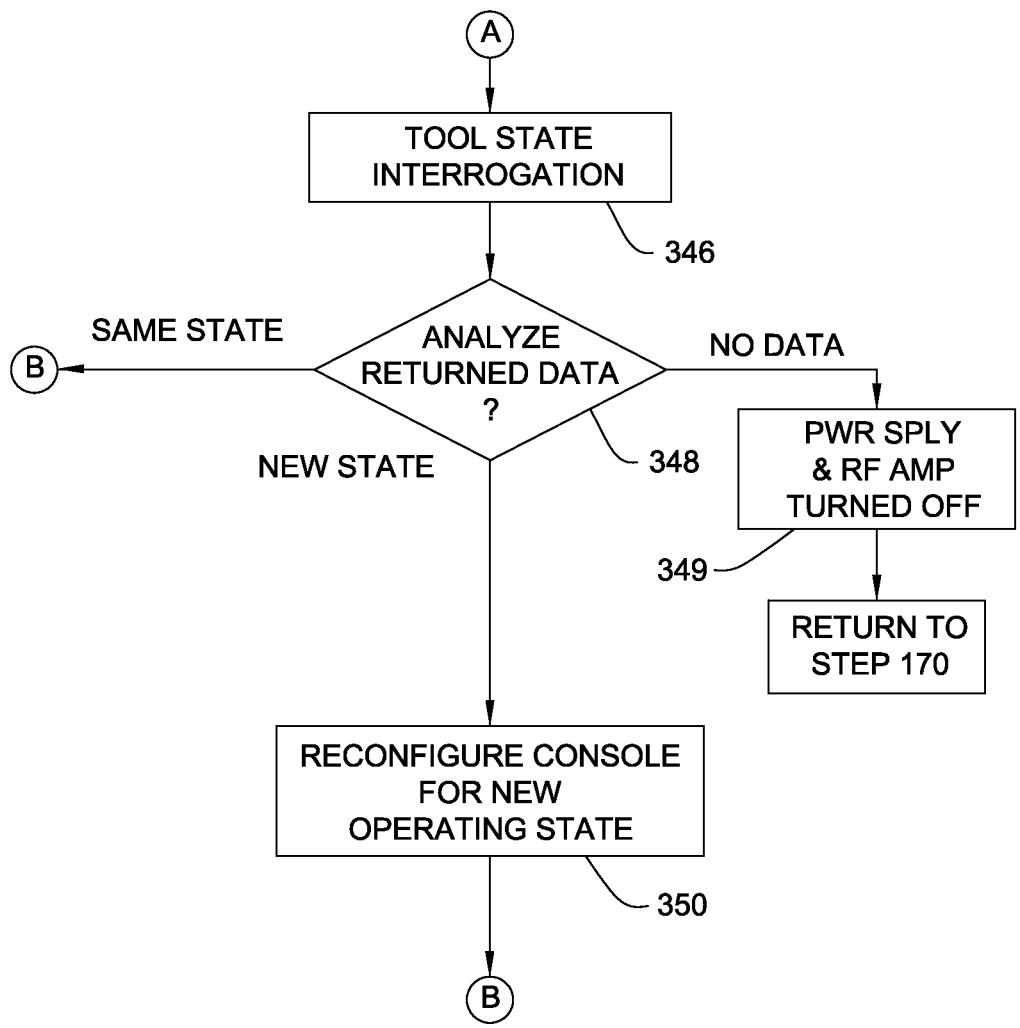
Figure 14:
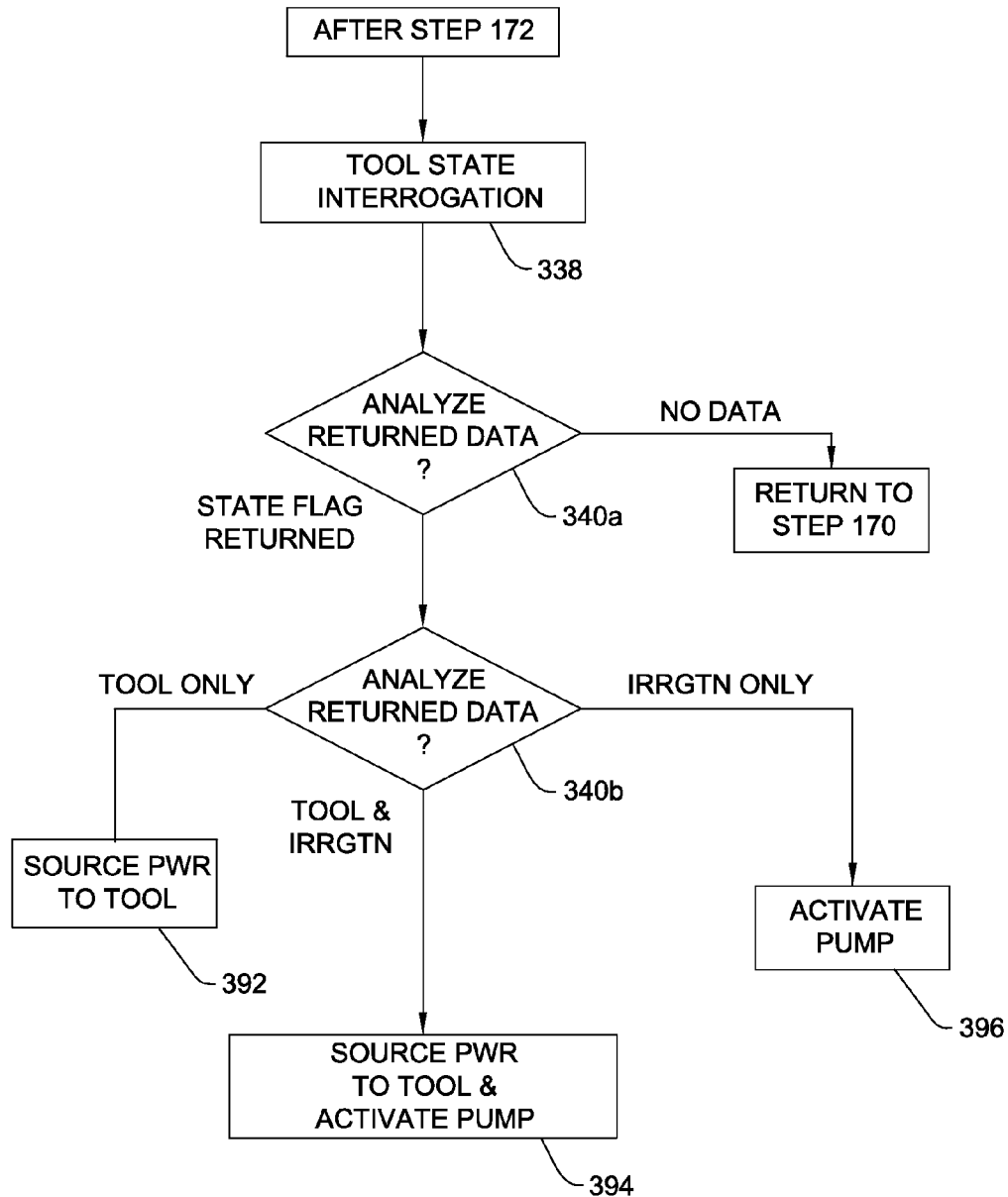
FIG. 14 is a flow chart of the process steps that may be executed so that system can simultaneously apply current to and irrigation tissue.

The steps described with respect to FIGS. 11A-11B are then executed in order to regulate actuation of the tool. When activation of the electrodes 34 or 36, and/or supply of irrigation fluid is needed, the practitioner depresses the appropriate one of the three switches 384, 386 or 388. The display controller 48 as a consequence of the execution of steps 338 and 340 analyzes the returned data to determine if one of the three switches was depressed. If none of the switches are depressed, the steps 330 and 342 are cyclically executed as before, step 340a in FIG. 14.

If the data returned are from memory 364, the display controller 48, in step 340b, recognizes that only activation of the electrodes is required. Accordingly, the display controller 48 issues instructions to the power supply 42 and RF controller 48 to causes the sourcing of power to the electrodes, step 392 of FIG. 14. If the data are returned from memory 370, the display controller 48 recognizes that simultaneous activation of the electrodes 34 and 36 the discharge or irrigation fluid is required. Display controller 48 therefore simultaneously asserts signals that cause the RF amplifier 44 to source power to the electrodes and that cause pump 294 to supply irrigation fluid to the tool conduit 358, step 394.

If the data returned are from memory 376, display controller 48 in step 340b. interprets these data as indicating only irrigation fluid is required. Accordingly, the display controller 48 only asserts the necessary signals to the pump controller 296 that result in the appropriate actuation of the pump 294, step 396.

While not illustrated, it should be appreciated that steps 338, 340a and 340b are executed will the system remains in the practitioner-desired mode operating state. As before, when these steps determine the practitioner wants the system placed in a new operating state, display controller 48 asserts or negates the appropriate signals.

It should be appreciated that tool 352 of this version of system of the invention does more than allow the practitioner to, with a single tool both supply electrical energy or irrigation fluid to the body site. The practitioner can, with the same hand that positions the tool at the site, control when the power and irrigation fluid are supplied. Further, the control mechanism allows the practitioner to supply the power or fluid or sequentially or simultaneously.

Again, it should be appreciated that tool 352 can be connected to a conventional console.

VI. Fourth Alternative Tool

Figure 15A:
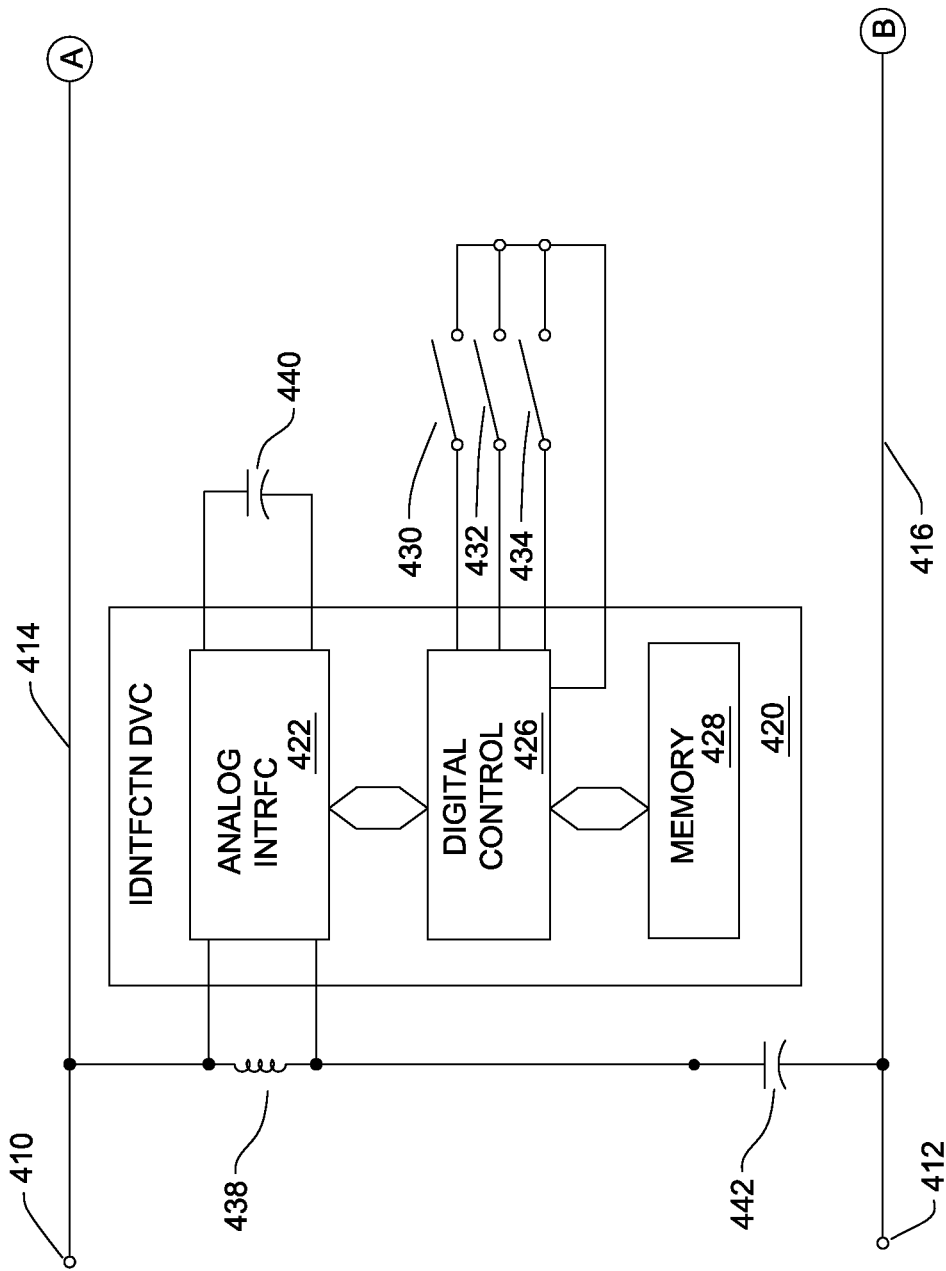

FIGS. 15A and 15B collectively illustrate an alternative powered surgical tool 402 constructed in accordance with this invention. Tool 402, instead of having electrodes across which currents are flowed, has a power generator 404. Power generator 404 converts the power sourced by the console to another form of energy. For example, power generator 404 may be: a motor that outputs mechanical energy; an RF generator; an ultrasonic vibrator; a device that outputs thermal energy or a device that generates photonic (light) energy. The energy output by the power generator 404 is administered to the appropriate tissue by a surgical/medical power applicator 406. Power applicator 406 is designed to apply the energy to the medical/surgical site to accomplish the desired therapeutic of diagnostic task. If the energy is mechanical energy, the power applicator can be a device such as a bur, a shaver or a drill. Electrodes or coils are two of the power application used to apply RF energy or thermal energy to a surgical site. A piezoelectric transducer can serve as both the power generator 404 and power applicator 406 for generating and applying ultrasonic energy to a treatment site. An optically transparent core can function as the power applicator 406 for a photonic energy-emitting power generator 404.

Power signals to the power generator 404 are sourced over conductors 414 and 416. Conductors 414 and 416 are analogous to conductors 92 and 96, respectively. Pins 410 and 412, connected to conductors 414 and 416, respectively, serve as the mechanical interface over which the cable conductors are connected to conductors 414 and 416. While not illustrated, it should be understood that tool 402 typically includes some sort of hand-held body to which the power cable is connected and that contains power generator 404 and conductors 414 and 416. Pins 410 and 412 or similar conductors are located at one end of the body. Power applicator 406 extends from the opposed end of the body.

Disposed inside the body of tool 402 is a tool and state identification device 420. Identification device 420 is similar to the previously described RFID 90. An analog interface 422 functions as the interface for the AC signals received and power sunk by device 420. A memory 428 contains data read out of the device 420. Between analog interface 422 and memory 428, identification device includes a digital control 426. Digital control 426, based in part on the digital signals extracted by analog interface 422, retrieves data from memory 428 and forwards the data signals to the analog interface 422. Based on the received data signals, analog interface 422 modulates the impedance of the circuit including device 420.

Also connected to digital control 426 are a set of switches 430, 432 and 434. Each switch 430, 432 and 434 opens/closes a connection to a reference voltage internal to the identification device 420. In some versions of the invention, each switch 430, 432 and 434 is normally in the open state. Separate buttons mounted to the tool body that can be depressed by thumb or finger of the hand holding the tool are used to actuate each switch 430, 432 and 434.

Tool 402 also includes an inductor 438 that is analogous to previously described inductor 98. Inductor 438 is connected to the opposed input pins of identification device 420. More particularly, these input pins are connected to the device analog interface 422. Capacitor 440, analogous to capacitor 102, represents the resonance capacitor internal to the device analog interface 422. Inductor 438 is shown as having one end connected to power signal conductor 414 internal to the tool 420. While not explicitly shown in FIG. 15A, it is understood that capacitor 440 is connected in series across inductor 438. It should also be understood that capacitor 440 is actually internal to analog interface 422.

Also internal to the body of tool 402 is a capacitor 442, analogous to capacitor 94. One end of capacitor 442 is connected to the end of inductor 438 opposite the end connected to conductor 414. The opposed end of capacitor 440 is connected to conductor 416.

The control console of the system of this invention used to activate tool 402 includes a power generating circuit capable of supplying the appropriate power signals to the power generator 404. These signals may be low frequency AC signals, for example below 1 MHz. In some versions of the invention, control console may be configured to source DC power signals to the power generator 404.

A system of this invention with tool 402 is operated in the same general manner in which the previously described versions of the invention operate. Inductor 438 and capacitors applies the interrogation signal received over terminals 410 and 412 to identification device 420 without an appreciable voltage drop while substantially reducing the voltage of the power signal applied to the identification device. Once the tool 402 is attached to the control console by a cable such as cable 38, interrogation signals are sent to the identification device 420 over the cable conductors over which the power signals are sourced. In response to these signals, identification device 420 outputs data signals detectable by the reader internal to the control console.

More particularly, the identification device digital control 426 retrieves from memory 428 a specific set of data signals based on the state of switches 430, 432 and 434. For example if the tool 402 is one used to perform both a procedure at a surgical site and that can also supply irrigation fluid, digital control 426 may cause data indicating a first tool operating state (handpiece and irrigation both off) if no switch is depressed, data indicating a second tool operating state (handpiece on, irrigation off) if switch 430 is depressed, a third operating state (handpiece off, irrigation on) if switch 432 is depressed and a fourth operating state (handpiece and irrigation both on) if switch 434 is depressed.

Controller 48 internal to the console, upon receipt of the particular state signal actuates the power generating circuit and/or irrigation pump 294 as appropriate.

Periodically during the sourcing of power signals to the tool power generator 404, interrogation signals are output by the memory reader 66. This process is similar to step 338 discussed above with respect to FIG. 11A. Again, these signals are output over the cable power conductors simultaneously with the sourcing of the powering signals. During the sourcing of the power signals, the practitioner will usually at once change the open/closed settings of switches 430-434. Accordingly, in response to one of these subsequent interrogations of the tool, the data returned will indicate the tool is to be placed on a different state. Console controller 48 adjusts the outputting of power signals and/or resets actuation of the irrigation pump based on the newly received state data.

The version of the invention described with respect to FIGS. 15A and 15B eliminates the need to provide a surgical tool with invention with duplicate identification devices that vary in the contents of the data stored by the devices.

VII. Alternative Embodiments

The above is directed to specific versions the surgical tool system of this invention. Other versions of this invention may have features different from what has been described. For example, in some versions of the invention, the control console may not include switched components such as relays to selectively disconnect the memory reader 66 from the RF amplifier circuit. In alternative versions of the invention, the isolation may comprise a circuit similar to the circuit internal into to the tool hub, to substantially reduce the extent to which the potential of the power signal from RF amplifier 44 is applied to the memory reader 66. Alternatively, capacitor 268 and inductor 270 of the version of the invention described with respect to FIG. 7 may function as the isolation circuit.

Similarly, the isolation circuit internal to the tool that substantially reduces the potential of the power signals from being applied across the memory integral with the tool may have constructions different from what has been described.

Likewise, it should be appreciated that the structure of the tools which are part of this system may vary from the depictions of the described tools. For example, a bipolar tool of this invention may include a single structural probe to which both the active and return electrodes are attached. Similarly, a tool may include plural electrodes that are electrically connected together. This type of tool can be considered to have plural active or plural return electrodes.

In some versions of the invention, the tool may be provided with sufficient memories and switches so, depending on which switch is depressed, the sourced power signal is one from a set of three or more power signals that could be sourced to the tool. For example, cut; fast coagulation; or slow coagulation. Also, the versions of the invention wherein the on tool controls allow control of the characteristics of the power signal sourced to the tool or regulation of the console pump 294 are not limited to bipolar tools. These control circuits can be built into monopolar tools of this invention. Further, by the inclusion of additional memories and alternative switch assemblies it should be appreciated a single tool of this invention could be provided that allows for both control of the characteristics of the power signal and the pump that supplies irrigation fluid.

Likewise, the tool may be simply provided with a single switch. This tool could be a tool similar to that of the first described tool that only has a single on sate. This switch, when activated causes the memory internal to the tool to read out a data message to the console instructing the console to source the power signal to the tool. By placing this switch on the tool, the practitioner can with a single hand, control the position of the tool and the tool on/off state. The need for the practitioner to use a foot switch or an out of sterile field assistant to actuate the tool would be eliminated.

The construction of the power signal generating components as well as the components that regulate the power generating components internal to the control may likewise vary from what has been described.

Similarly, there is no requirement that in all versions of the invention that the pump 294 and its regulator 296 be built into the console from which the power signals are sourced. In some versions of the invention, pump 294 and regulator 296 are built into a stand alone unit configured to receive instruction signals from display controller 48.

As mentioned above the system of this invention may be constructed to power medical and surgical tools other than electrosurgical tools. These tools each include an isolation circuit that prevents application of the sourced power signals to the tool memory. This isolation circuit can be as simple as an inductor, if the sourced power is a DC signal or a very low frequency AC signal. In these versions of the invention, the isolation circuit is configured to substantially reduce the potential of signals applied to the tool memory when the signals have a frequency at least two times the frequency of the interrogation signal. Alternatively, a capacitor can function as the isolation circuit if the sourced power is a high frequency AC signal. In these versions of the invention, the interrogation signal applied to the identification device is at a frequency appreciably lower than the frequency of the power signal. In these versions of the invention, the isolation circuit is configured to substantially reduce the potential of signals applied to the tool memory when the power signals have frequencies of less one-half the frequency of the interrogation signal. In some versions of the invention, to ensure proper bypassing of the sourced power signals from the identification circuit the power signals and interrogation signals should have frequencies that are different by a factor of at least 10. In other words, the frequency of one of the power signal or the interrogation signal should be at least 10 times that of the other of, respectively, the interrogation signal or the power signal.

Both the tool and console isolation circuits may have different components if it designed to selectively pass through to or isolation signals from the tool memory (or memory reader) based on characteristics other than signal frequency. For example, in some versions of the invention, the isolation circuit may be designed to pass through or block signal based on signal potential, frequency shift, amplitude shift, phase shift, or impedance shift.

The tool and console isolation circuits may also have different components if the characteristics of the signal the circuit is designed to substantially effect are different than signal potential. These characteristics include signal frequency, frequency shift, amplitude shift, phase shift, or impedance shift.

Further, it should be appreciated that the arrangement of FIGS. 15A and 15B can be incorporated into an electrosurgical tool constructed in accordance with this invention. Thus, the plural switches of this embodiment of the invention could be used to control not just if power signals are sourced to the tool electrodes but if the sourced signals are used in current flows used to facilitate tissue cutting or coagulation.

Similarly, the multi-memory assemblies may be incorporated into powered surgical tools other than electrosurgical tools.

Also, a tool may be constructed in accordance with this invention in which the identification device causes different data to be returned based on an input other than the open/closed state of one or more switches. Thus, in one alternative version of the invention, the plural switches can be replaced by a single multi-state switch. Circuitry internal to the tool and/or the identification device digital control monitors the state of the switch. Based on the switch state, the digital control 426 causes data representative of the switch state to be returned to the control console in response to the interrogation signal.

Figure 16:
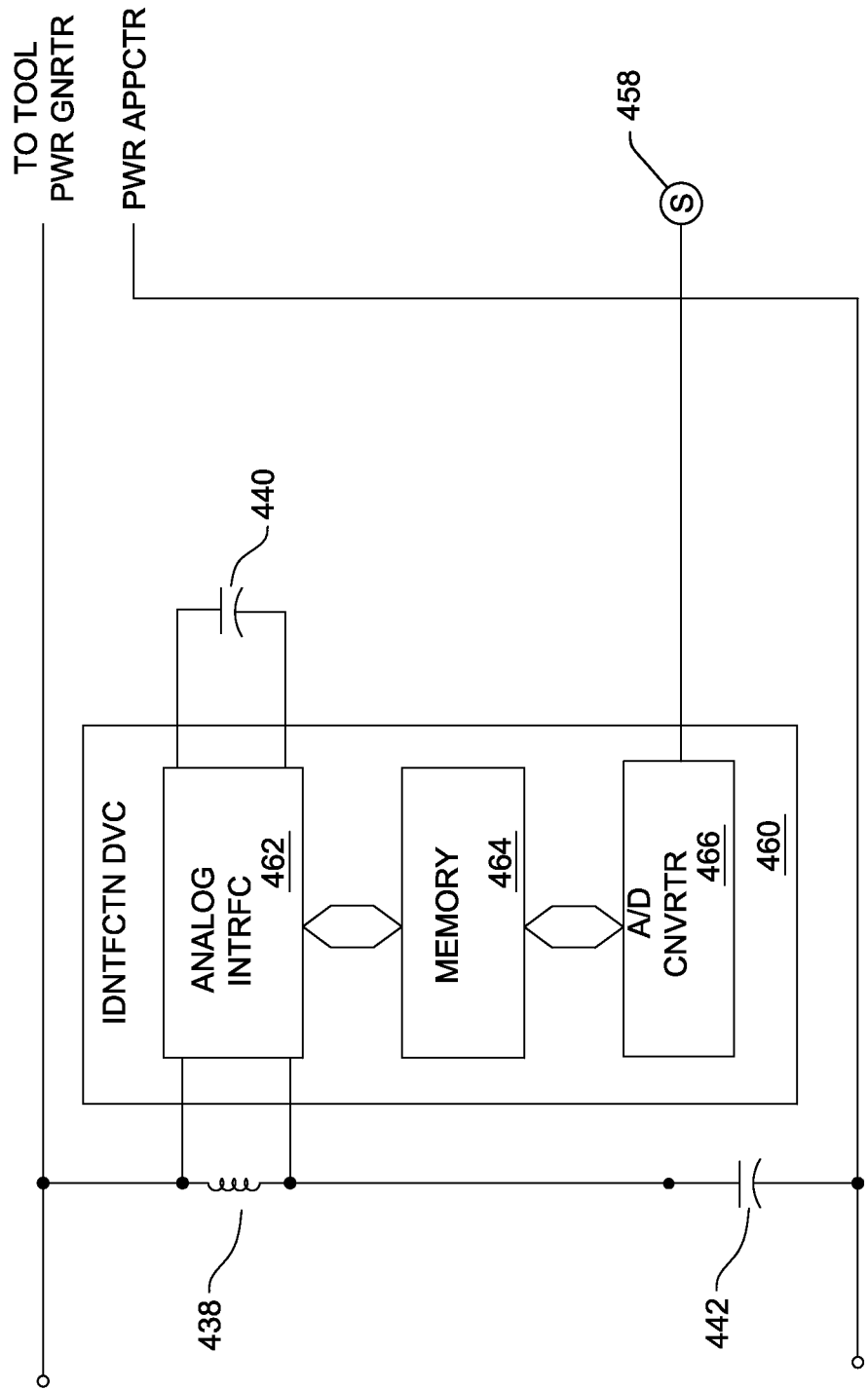
FIG. 16 is a block diagram of an alternative features that can be integrated into the tool of FIGS. 15A and 15B.

Alternatively, a tool of the system of this invention may include some type of analog sensor 460 as seen in FIG. 16. The sensor could for example be temperature sensitive transducer. Still another sensor may be device capable of monitoring blood oxygen. In some versions of the invention, the analog sensor generates a variable signal based on the state of a variable user-actuated control member attached to the tool. A digital-to-analog signal 466 integral with the identification device 460 generates a digital signal representative of the sensed parameter or sensed control member state. This digitized signal is stored in the memory 464 also part of the identification device. In response to the interrogation signal, the identification device 460 writes out a reply that includes the digitized representation of the sensor signal.

Alternatively, in response to the output signal from the sensor, the memory 464, which may include a logic circuit, selects select data for writing out in response to the interrogation signal In versions of the invention wherein the tool system is an electrosurgical tool system, it may not even be necessary to provide either the control console or the tool itself with an isolation circuit. This is because, owing to the characteristics of some RF tool power signals and the structures of the console memory readers and tool memories, the tool power signals do not have any adverse effect on the memory readers or tool memories.

Therefore, it is an object of the appended claims to cover all such variations and modifications that come within the true spirit and scope of the invention.

What is claimed is:

1. A powered surgical tool, said tool including:
    a body;
    terminal components attached to said body for releasably receiving a cable and to which an AC power signal from the cable is applied for actuating said tool;
    a power applicator attached to said body designed for application to tissue to perform a therapeutic or diagnostic task upon the application of the AC power signal to said terminal components; and
    a memory attached to said body, said memory storing data describing characteristics of the power signal applied to said tool, said memory configured to, in response to an AC interrogation signal, write out the data stored in said memory; and
    an isolation circuit connected between said memory and at least one said terminal component to which the power signal is applied, said isolation circuit configured to:
        when a signal having the characteristics of memory interrogation signal is applied to said terminal components, apply the signal to said memory without appreciably changing the characteristics of the signal; and
        when a signal having characteristics different from the characteristics of the interrogation signal is applied to said terminal components, substantially change the characteristics of the signal applied to said memory so that the changed signal applied to said memory does not adversely affect said memory and wherein, said memory and said isolation circuit are collectively configured so that said memory writes out the data stored therein over said isolation circuit through said at least one terminal component to which the power signal is applied.

2. The powered surgical tool of claim 1, wherein:
the interrogation signal applied to said memory through said terminal components is at a select frequency; and
said isolation circuit is configured to, when a signal at a frequency different from the frequency of the interrogation signal is applied to said terminal components, substantially reduce the potential of the signal applied to said memory.

3. The powered surgical tool of claim 1, wherein:
said power applicator is at least one electrode intended for application for tissue;
a conductor extends from at least one said terminal component over which the power signal applied to said at least one electrode; and
said isolation circuit is connected to said conductor.

4. The powered surgical tool of claim 1, wherein:
a power generator is mounted to said body and said power signal is applied to said power generator;
said power applicator is connected to said power generator and said power generator is configured to, upon application of the power signal to said power generator, activate said power applicator;
a conductor extends from at least one said terminal component over which the power signal applied to said power generator; and
said isolation circuit is connected to said conductor that extends between the said at least one terminal component and said power generator.

5. The powered surgical tool of claim 4, wherein said power generating unit includes one from the group consisting of: a motor; an RF generator; an ultrasonic vibrator; a device that outputs thermal energy; and a device that outputs photonic energy.

6. The powered surgical tool of claim 1, wherein:
a plurality of separate memories are attached to said body; and
at least one switch is attached to said body for selectively establishing a connection between one of said memories and, through said isolation circuit, at least one said terminal component.

7. The powered surgical tool of claim 1, wherein:
at least one switch is attached to said body; and
a control circuit is attached to said body, said control circuit configured to: monitor the state of said switch; and, in response to the state of said switch control which data in said memory are written out of said memory.

8. The powered surgical tool of claim 1, wherein:
said memory includes a pair of inputs to which said interrogation signal is applied and from which data are written out of said memory; and
said isolation circuit includes an inductor that is connected across the memory inputs.

9. The powered surgical tool of claim 1, wherein:
said memory includes at least one input to which said interrogation signal is applied and from which data are written out of said memory; and said isolation circuit includes a capacitor that is connected between one of said terminal components to which the power signal is applied and the memory input.

10. The powered surgical tool of claim 1, wherein:
said memory is part of an identification device;
said tool includes a sensor that monitors a biological parameter or the state of a user-actuated member, and that generates a variable sensor signal as a function of the monitored parameter or the state of the user-actuated member; and
said identification device is configured to receive the sensor signal and to output over at least one of said terminal components to which the power signal is applied a signal based on the sensor signal.

11. A powered surgical tool, said tool including:
a body;
at least one terminal attached to said body that is configured for releasable connection to a power supply that is separate from said tool for receiving from the power supply an AC power signal;
a power generating unit attached to said body that is connected to said at least one terminal to which the power signal is applied for receiving the AC power signal and outputting energy that is applied to a patient to perform a medical/surgical procedure;
a memory attached to said body, said memory containing data describing characteristics of said tool, said memory configured to, in response to an AC interrogation signal at a given frequency, write out the data stored in said memory;
an isolation circuit that extends between said at least one terminal to which the power signal is applied and said memory, said isolation circuit configured to:
when an AC signal having a frequency of the frequency of the interrogation signal is applied to the at least one terminal, apply the signal to said memory without appreciably changing the characteristics of the signal;
when an AC signal having a frequency that is at least one of less than one-half the frequency of the interrogation signal or more than two times the frequency of the interrogation signal is applied to the at least one terminal to which the power signal is applied, change the characteristics of the signal applied to said memory so that the signal applied to the memory does not adversely affect the memory; and
allow data written out of said memory to be accessed over said isolation circuit from the at least one terminal to which the power signal is applied.

12. The powered surgical tool of claim 11, wherein said isolation circuit is configured to change the characteristics of the signal applied to the memory from the at least one terminal to which said power signal is applied by reducing the potential of the signal.

13. The powered surgical tool of claim 11, wherein said at least one terminal to which said power signal is applied is configured to be releasably attached to a conductor internal a cable, the cable conductor extending from the power supply to said tool body for supplying the power signal to said power generating unit.

14. The powered surgical tool of claim 11, wherein said isolation circuit includes an inductor that is connected to said memory.

15. The powered surgical tool of claim 11, wherein said isolation circuit includes a capacitor that is connected to said memory.

16. The powered surgical tool of claim 11, wherein said power generating unit includes one from the group consisting of: a motor; an RF generator; an ultrasonic vibrator; a device that outputs thermal energy; an electrode that applies the power signal to tissue; and a device that outputs photonic energy.

17. The powered surgical tool of claim 11, further including a power applicator that is attached to said body for receiving the energy output by said power generating unit and applying the energy to the patient.

18. A powered surgical tool, said tool including:
a body;
at least one terminal attached to said body that is configured for releasable connection to a power supply that is separate from said tool for receiving from the power supply an AC power signal;
a power generating unit attached to said body that is connected to said at least one terminal for receiving the AC power signal and outputting energy that is applied to a patient to perform a medical/surgical procedure;
a memory attached to said body and that is connected to said at least one terminal to which the power signal is supplied to said body, said memory containing data that describing characteristics of said tool, said memory having two inputs across which AC signals are applied so that, in response to an interrogation signal, said memory writes out data over the inputs; and
an isolation circuit disposed in said body, said isolation circuit being connected between said at least one terminal that receives the power signal and said memory, said isolation circuit including an inductor that extends between the inputs of said memory and said isolation circuit configured to:
when a signal having the characteristics of memory interrogation signal is applied to said at least one terminal that receives the power signal, apply the signal to said memory without appreciably changing the characteristics of the signal;
when a signal having characteristics different from the characteristics of the interrogation signal is applied to said at least one terminal that receives the power signal, substantially change the characteristics of the signal applied to said memory so that the changed signal applied to said memory does not adversely affect the memory; and
allow the data read from said memory to be read out across said isolation circuit through said at least one terminal that receives the power signal.

19. The powered surgical tool of claim 18, wherein said isolation circuit further includes at least one capacitor that is connected to at least one input of said memory.

20. The powered surgical tool of claim 18, wherein said isolation circuit includes a capacitor that is in parallel with said inductor.

21. The powered surgical tool of claim 20, wherein said capacitor that is parallel with said inductor is located in said memory.

22. The powered surgical tool of claim 18, wherein:
said memory is configured to exchange signals with a memory reader at a select frequency; and
said isolation circuit includes a capacitor that is parallel with said inductor of said isolation circuit so as to form a tank circuit with said inductor that has a resonant frequency that is offset from the frequency at which said memory exchanges signals with the memory reader.

23. The powered surgical tool of claim 18, wherein said at least one terminal that receives the power signal is configured to be releasably attached to a conductor internal to a cable, the cable conductor extending from the power supply to said tool body for supplying the power signal to said power generating unit.

24. The powered surgical tool of claim 18, wherein said power generating unit includes one from the group consisting of: a motor; an RF generator; an ultrasonic vibrator; a device that outputs thermal energy; an electrode that applies the power signal to tissue; and a device that outputs photonic energy.

25. The powered surgical tool of claim 18, further including a power applicator that is attached to said body for receiving the energy output by said power generating unit and applying the energy to the patient.

26. The powered surgical tool of claim 18, wherein said isolation circuit further includes: a first capacitor connected in parallel across said inductor; and a second capacitor connected in series with said inductor.

27. The powered surgical tool of claim 18, wherein said memory is part of an RFID tag.

* * * * *